US010465226B2

(12) United States Patent
Hasan et al.

(10) Patent No.: US 10,465,226 B2
(45) Date of Patent: Nov. 5, 2019

(54) DEVICES AND METHODS FOR TARGET ANALYTE DETECTION IN LIQUID SAMPLES

(71) Applicant: THE GENERAL HOSPITAL CORPORATION, Boston, MA (US)

(72) Inventors: Tayyaba Hasan, Boston, MA (US); Akilan Palanisami, Boston, MA (US); Shazia Khan, Boston, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 0 days.

(21) Appl. No.: 15/519,340

(22) PCT Filed: Oct. 16, 2015

(86) PCT No.: PCT/US2015/055931
§ 371 (c)(1),
(2) Date: Apr. 14, 2017

(87) PCT Pub. No.: WO2016/061453
PCT Pub. Date: Apr. 21, 2016

(65) Prior Publication Data

US 2017/0233785 A1 Aug. 17, 2017

Related U.S. Application Data

(60) Provisional application No. 62/064,513, filed on Oct. 16, 2014.

(51) Int. Cl.

| | |
|---|---|
| ***C12Q 1/14*** | (2006.01) |
| ***B01L 3/00*** | (2006.01) |
| ***G01N 33/569*** | (2006.01) |
| ***G01N 33/58*** | (2006.01) |

(52) U.S. Cl.
CPC .............. *C12Q 1/14* (2013.01); *B01L 3/5025* (2013.01); *B01L 3/5027* (2013.01); *B01L 3/502715* (2013.01); *B01L 3/502746* (2013.01); *G01N 33/56938* (2013.01); *G01N 33/582* (2013.01); *B01L 2300/042* (2013.01); *B01L 2300/044* (2013.01); *B01L 2300/0681* (2013.01); *B01L 2300/0874* (2013.01); *B01L 2300/0887* (2013.01); *B01L 2300/12* (2013.01); *B01L 2400/049* (2013.01)

(58) Field of Classification Search
CPC ................................................ G01N 33/56938
See application file for complete search history.

(56) References Cited

U.S. PATENT DOCUMENTS

| | | | |
|---|---|---|---|
| 3,765,577 | A | 10/1973 | Burns |
| 5,236,826 | A | 8/1993 | Marshall |
| 5,624,850 | A | 4/1997 | Kumar et al. |
| 5,705,338 | A | 1/1998 | Piran et al. |
| 2006/0046305 | A1 | 3/2006 | Liu et al. |
| 2010/0129922 | A1 | 5/2010 | Gold et al. |
| 2011/0112059 | A1 | 5/2011 | Hasan et al. |
| 2012/0159761 | A1 | 6/2012 | Fetvedt |

OTHER PUBLICATIONS

Varshney et al. Transactions of ASABE, 2006, 49(6):2061-2068.*
Yamaguchi, et al., Applied and Environmental Microbiology, 2011, 1536-1539.*
Khan et al. Abstract of the 37th Meeting of the American Society for Photobiology, 2014, p. 85.*
Herr et al., PNAS., 2007, 104(13):5268-5273.*
International Search Report for Application No. PCT/US15/55931 dated Jan. 5, 2016.

* cited by examiner

*Primary Examiner* — Bin Shen
(74) *Attorney, Agent, or Firm* — Tarolli, Sundhheim, Covell & Tummino LLP

(57) ABSTRACT

One aspect of the present disclosure relates to a device for detecting a target analyte in a liquid sample. The device can comprise a housing. The housing can include an inlet for receiving a liquid sample, an outlet for removing a volume of the liquid sample from the device, a filter associated with the outlet and being sized and dimensioned to retain a target analyte on a surface thereof, and a flow system comprising at least one channel that is in communication with the inlet and the outlet. At least a portion of the at least one channel can be located substantially adjacent the surface of the filter and be shaped and dimensioned to reduce the amount of unreacted fluorescent probe available to create the background interference during detection of the target analyte.

8 Claims, 22 Drawing Sheets

DEVICES AND METHODS FOR TARGET ANALYTE DETECTION IN LIQUID SAMPLES

RELATED APPLICATION

This application claims the benefit of U.S. Provisional Patent Application Ser. No. 62/064,513, filed Oct. 16, 2014, the entirety of which is hereby incorporated by reference for all purposes.

TECHNICAL FIELD

The present disclosure relates generally to devices and methods for detecting a target analyte in a liquid sample and, more particularly, to highly sensitive and specific microfluidic devices and methods for rapidly detecting a target analyte in a liquid sample.

BACKGROUND

To diagnose disease, biological samples (e.g., blood, urine, wound tissue, etc.) are tested for pathogens, with the ultimate goal of determining the most effective treatment for a particular disease and monitoring the progression of the disease in the patient. Low quantities of pathogen in biological samples make their detection difficult to perform rapidly, cheaply and accurately. Detection is additionally confounded by other non-pathogens in the sample (e.g., red blood cells, dust) that can reduce the signal-to-background ratio during pathogen detection. Traditional methods for overcoming these drawbacks are growth-based (e.g., multiplying the pathogen for 12-16 hours so they can be easily detected followed by further testing of pathogen characteristics) or DNA-based. Such growth-based methods are slow and expensive, while the DNA-based tests, which are more rapid than the growth-based methods, are comparatively more expensive and, being genotypic, may not predict phenotypic relevance.

SUMMARY

The present disclosure relates generally to devices and methods for detecting a target analyte in a liquid sample and, more particularly, to highly sensitive and specific microfluidic devices and methods for rapidly detecting a target analyte in a liquid sample.

One aspect of the present disclosure relates to a device for detecting a target analyte in a liquid sample. The device can comprise a housing. The housing can include an inlet for receiving a liquid sample, an outlet for removing a volume of the liquid sample from the device, a filter associated with the outlet and being sized and dimensioned to retain a target analyte on a surface thereof, and a flow system comprising at least one channel that is in communication with the inlet and the outlet. At least a portion of the at least one channel can be located substantially adjacent the surface of the filter and be shaped and dimensioned to reduce the amount of unreacted fluorescent probe available to create the background interference during detection of the target analyte.

Another aspect of the present disclosure relates to a method for detecting a target analyte in a liquid sample. One step of the method can include introducing, through an inlet of a device, a liquid sample either before, during, or after introduction of a detection reagent through the inlet. A volume of the liquid sample can be removed from an outlet of the device to cause a target analyte, if present, to be retained on a surface of a filter associated with the outlet. Next, the presence of the target analyte can be determined in the liquid sample.

Another aspect of the present disclosure relates to a method for detecting a target pathogen, or biomolecule associated therewith, in a liquid sample. One step of the method can include introducing, through an inlet of a device, a liquid sample either before, during, or after introduction of a fluorescent probe specific to the target pathogen, or biomolecule associated therewith, through the inlet. A volume of the liquid sample can be removed from an outlet of the device to cause a target pathogen, or biomolecule associated therewith, if present, to be retained on a surface of a filter associated with the outlet. A release mechanism of the device can then be actuated to cause release of the retained target pathogen, or biomolecule associated therewith, off of the surface of the filter. Next, the presence of the target pathogen, or biomolecule associated therewith, can be determined by fluoroscopy in the liquid sample. Release of the target pathogen, or biomolecule associated therewith, can reduce background fluorescence associated with the fluorescent probe during the determining step.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Definitions

Figure 1:
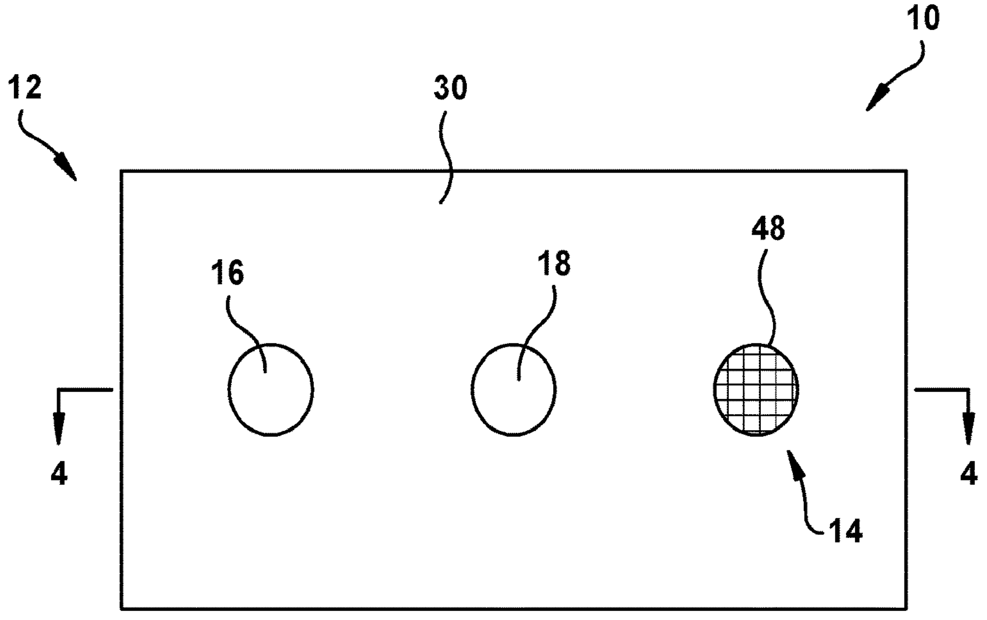
FIG. 1 is a schematic illustration showing an upper surface of a device for detecting a target analyte in a liquid sample constructed in accordance with one aspect of the present disclosure.
Figure 2:
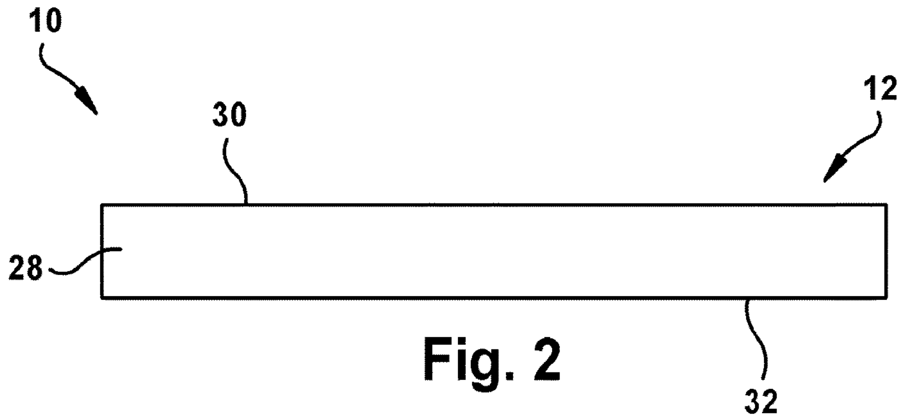
FIG. 2 is a schematic illustration showing a side surface of the device in FIG. 1.

Unless defined otherwise, all technical and scientific terms used herein have the same meaning as is commonly understood by one of skill in the art to which the present disclosure pertains.

In the context of the present disclosure, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

As used herein, the terms "about" or "approximately" can generally mean within 20 percent, preferably within 10 percent, and more preferably within 5 percent of a given value or range. Numerical quantities given herein are approximate, meaning that the term "about" or "approximately" can be inferred if not expressly stated.

As used herein, the term "target analyte" can refer to a substance in a liquid sample capable of being detected and analyzed by the present disclosure. Target analytes can include, but are not limited to, molecules, peptides, proteins (including prions), nucleic acids, oligonucleotides, cells, microorganisms or pathogens (e.g., viruses, bacteria, fungi), fragments of microorganisms or pathogens, products or biomolecules associated with microorganisms or pathogens (e.g., enzymes or metabolic products produced by a microorganism or pathogen), enzyme substrates, ligands, carbohydrates, hormones, sugar, cofactors, pollutants, chemical agents, small molecules, drugs, toxins, plants and fragments and products thereof, biomarkers indicative of a disease or disorder, and any substance for which attachment sites, binding members, or receptors can be developed.

As used herein, the term "biomolecule" can refer to any molecule produced by a living organism including, but not limited to, proteins, peptides, polysaccharides, nucleic acids, carbohydrates, lipids, as well as analogs and fragments thereof. A biomolecule associated with a pathogen, for example, can refer to any molecule or substance produced by the pathogen. The term "biomolecule" can also refer to any molecule or substance produced by, or formed as the result of, the action or activity of a biomolecule that was initially produced by a living organism.

As used herein, the term "liquid sample" can refer to any quantity of a liquid or fluid that contains, or is suspected of containing, one or more target analytes. A liquid sample, for instance, can be extracted from a biological sample derived from humans, animals, plants, fungi, yeast, bacteria, tissue cultures or viral cultures, blood cultures (e.g., with or without antibiotics), throat swabs, or a combination of the above. In some instances, a liquid sample can comprise a bodily fluid, such as serum, serum, buffy coat, saliva, whole blood, partially processed blood, nasopharyngeal fluid (e.g., sinus drainage), wound exudates, pus, lung and other respiratory aspirates, bronchial lavage fluids, medial and inner ear aspirates, cyst aspirates, cerebrospinal fluid, stool, diarrheal fluid, tears, mammary secretions, ovarian contents, ascites fluid, mucous, gastric fluid, gastrointestinal contents, urethral discharge, peritoneal fluid, meconium, vaginal fluid or discharge, amniotic fluid, semen, penile discharge, synovial fluid, urine, sputum, seminal or lymph fluids, or the like. A liquid sample can be first processed (e.g., purified or partially purified) and/or mixed with buffers and/or reagents used to generate appropriate assay conditions.

As used herein, the term "subject" can refer to any warm-blooded organism including, but not limited to, human beings, pigs, rats, mice, dogs, goats, sheep, horses, monkeys, apes, rabbits, cattle, etc. The term "subject" can also be used interchangeably herein with the term "patient".

As used herein, the term "electrical communication" can refer to the ability of a generated electric field to be transferred to, or have an effect on, one or more components of the present disclosure. In some instances, the generated electric field can be directly transferred to a component (e.g., via a wire or lead). In other instances, the generated electric field can be wirelessly transferred to a component.

As used herein, the term "in fluid communication" can refer to a fluid (e.g., a liquid) that can move from one part of a device to another part of the device. Two or more parts of the device can be in fluid communication by being physically linked together or adjacent one another, or the fluid communication can be mediated through another part of the device.

As used herein, the term "coupled" can refer to direct coupling or indirect coupling via a separate object. The term can also encompass two or more components that are continuous with one another by virtue of each of the components being formed from the same piece of material. Also, the term "coupled" may include chemical, mechanical, thermal or electrical coupling. Fluid coupling can mean that fluid is in communication between designated parts or locations.

As used herein, the terms "detection reagent", "probe", "label", "tag", and "marker" can be used interchangeably and refer to a molecule or composition of molecules that is detectable by optical, spectroscopic, photochemical, biochemical, immunological, chemical or magnetic means, and is typically bound or complexed with a target analyte. Detection reagents can include, but are not limited to, colored, radioactive, fluorescent, ultraviolet, or magnetic molecules or particles capable of binding to a target analyte and/or conjugated to other molecules or particles (e.g., antibodies) known to bind to a target analyte. One example of a detection reagent can include a fluorescence quenching-based probe, such as beta-Lactamase Enzyme Activated Fluorophore (beta-LEAF). Other examples of detection reagents, their targets, and their respective concentrations in the devices and methods described herein are presented in Table 1 below.

TABLE 1

| Class | Examples | Target | Concentration |
|---|---|---|---|
| β-LEAF | | B-lactamase | 100 nM-100 μM |
| Oxygen sensitive probe | Tris(4,7-diphenyl-1,10-pheanthroline)ruthenium dichloride<br>Tris(4,7-diphenyl-1,10-pheanthroline)ruthenium hexafloride | Aerobic metabolism | 100 nM-100 μM |
| pH sensitive probe | SnArf (Thermoscientific)<br>Fluorescein<br>PHrodo (Thermoscientific) | Anaerobic respiration | 100 nM-100 μM |
| Gram status | Hexidium bromide<br>Fluorescent wheat germ agglutinin | Cell wall | 100 nM-10 μM |
| Immune cell typing | Antibodies | Membrane markers | 100 nM-10 μM |

As used herein, the term "reagent" can refer to any chemical or biochemical agent used in a reaction, including enzymes. A reagent can include a single agent or a mixture of two or more agents.

As used herein, the term "point-of-care environment" can refer to real-time diagnostic testing that can be done in a rapid time frame so that the resulting test is performed faster than comparable tests that do not employ the present disclosure. Point-of-care environments can include, but are not limited to: emergency rooms; at a bedside; in a stat laboratory; operating rooms; hospital laboratories and other clinical laboratories; doctor's offices; in the field; or in any situation or locale where a rapid and accurate result is desired.

Overview

The present disclosure relates generally to devices and methods for detecting a target analyte in a liquid sample and, more particularly, to highly sensitive and specific microfluidic devices and methods for rapidly detecting a target analyte in a liquid sample. Conventional techniques and associated diagnostic devices for detecting pathogens (e.g., bacteria) in blood require a full microbiological laboratory and entail a lengthy process of partially classifying the particular pathogen followed by subsequent culture before accurate detection can be done. Unlike conventional techniques, the present disclosure captures and concentrates pathogens, or biomolecules associated therewith, for direct detection and either reduces or obviates the need to incubate or culture the pathogens prior to detection. Additionally, the present disclosure can significantly reduce background interference and thereby increase resolution of a signal (e.g., a fluorescence signal) being detected. Advantageously, the present disclosure provides rapid, point-of-care pathogen detection with exceptional sensitivity and specificity, thereby allowing a clinician or other medical professional to quickly guide treatment. These and other advantages of the present disclosure are discussed in more detail below.

Devices

One aspect of the present disclosure can include a device 10 (FIGS. 1-4) for detecting a target analyte in a liquid sample. The device 10 can generally comprise a housing 12 and an optional release mechanism 14 coupled to the housing. The housing 12 can include an inlet 16 for receiving a liquid sample, an outlet 18 for removing a volume of the liquid sample from the device 10, a filter 20 associated with the outlet and being sized and dimensioned to retain a target analyte on a surface 22 thereof, and a flow system 24 comprising at least one channel 26 that is in communication with the inlet and the outlet. The release mechanism 14 can be in communication with the at least one channel 26. The release mechanism 14 can also be configured to permit selective release of the retained target analyte off of the surface 22 of the filter 20 for detection of the target analyte. Although the device 10 is described below as having a single inlet 16, a single outlet 18, a single channel 26, and a single release mechanism 14 (a "single channel device"), it will be appreciated that the device can have any number, combination, and arrangement of inlets, outlets, channels, and release mechanisms (a "multi-channel device"), for example, to facilitate high-throughput analysis).

In some instances, the device 10 can be configured as a single, standalone platform for detecting a target analyte that is free from physical connection to any other apparatus or devices. In other instances, multiple devices 10 can be formed or located on a substrate (e.g., a plastic sheet) such that the substrate defines a plurality of sections, each of which includes a device of the present disclosure. In such instances, each section can be selectively removed (e.g., broken off) from the substrate as needed for analysis. Alternatively, the substrate could be processed using an automated machine for multiplex analysis.

In further instances, the device 10 can comprise a microfluidic device. By "microfluidic" it is meant that the flow system 24 of the device 10 can include one or more sets of channels 26 that interconnect to form a generally closed microfluidic network. Generally, microfluidic channels can include fluid passages having at least one internal cross-sectional dimension that is less than about 500 μm (e.g., typically between about 0.1 μm and about 500 μm) and/or a height or width of less than about 200, 100 or 50 μm. Such a microfluidic network may include one, two, or more openings at network termini, or intermediate to the network that interface with the external environment. Such openings may receive, store, and/or dispense a liquid. A microfluidic device may also include any other suitable features or mechanisms that contribute to liquid, reagent, and/or target analyte manipulation or analysis. For example, a microfluidic device may include regulatory or control mechanisms (e.g., valves and/or pumps) that determine aspects of liquid flow rate and/or path. Alternatively or additionally, a microfluidic device may include mechanisms (e.g., heaters, coolers, electrodes, lenses, gratings, light sources, pressure sensors, pressure transducers, microprocessors, microelectronics, etc.) that determine, regulate, and/or sense liquid temperature, fluid pressure, flow rate, exposure to light, exposure to electric fields, magnetic field strength, and/or the like. Furthermore, a microfluidic device can include one or more features (e.g., any detectable shape or symbol, or set of shapes or symbols, such as black-and-white or colored barcode, a word, a number, and/or the like, that has a distinctive position, identity, and/or other property) that act as a code to identify a particular target analyte.

In another aspect, the housing 12 of the device 10 can include any one or combination of structures configured to at least partially enclose the device components. Thus, the housing 12 can comprise several separate components or it may be formed as a unitary structure. The housing 12 can comprise a solid, semi-solid, or flexible substrate made from one or a combination of materials having sufficient physical strength, and being capable of being shaped into, the required physical and functional appearance. In one example, the housing 12 can be made from one or a combination of materials including, but not limited to, silicon, silcon dioxide, silicon nitride, glass and fused silica, gallium arsenide, indium phosphide, aluminum, ceramics, polyimide, quartz, plastics, resins and polymers including polymethylmethacrylate, acrylics, polyethylene, polyethylene terepthalate, polycarbonate, polystyrene and other styrene copolymers, polypropylene, polytetrafluoroethylene, superalloys, zircaloy, steel, gold, silver, copper, tungsten, molybdeumn, tantalum, KOVAR, KEVLAR, KAPTON, MYLAR, brass, sapphire, etc. The material(s) used for the housing 12 should be sufficiently robust to facilitate storage, transport, and use of the device 10. In some instances, the material(s) used to form the housing 12 can be compatible with reagents associated with use of the device 10. For example, if any reagents are prearranged in the device 10, the material(s) must be compatible with the reagents so that the reagents cannot dissolve, react with, or diffuse into the material(s) within a predetermined period of time.

The housing 12 can be made in a variety of ways. Suitable fabrication techniques will depend on the choice of substrate, but suitable methods can include, but are not limited to, a variety of micromachining and microfabrication techniques, including film deposition processes such as spin coating, chemical vapor deposition, laser fabrication, photolithographic and other etching techniques using either wet chemical processes or plasma processes, embossing, injection molding and bonding techniques. In addition, there are printing techniques for the creation of desired fluid guiding pathways; that is, patterns of printed material can permit directional fluid transport. Thus, the build-up "ink" can serve to define a flow channel. In addition, the use of different "inks" or "pastes" can allow different portions of channels 26 having different flow properties.

The substrate comprising the housing 12 can be configured to handling a single liquid sample that may contain a plurality of target analytes. That is, a single liquid sample can be added to the device 10 and the sample may either be aliquoted for parallel processing for detection of the target analytes, or the sample may be processed serially, with individual target analytes being detected in a serial fashion. In addition, liquid samples may be removed periodically or from different locations for in-line sampling. In other instances, the substrate comprising the housing 12 can be configured for handling multiple liquid samples, each of which may contain one or more target analytes. In such instances, each liquid sample can be handled individually; that is, the manipulations and analyses are done in parallel, with no contact or contamination between them. Alternatively, there may be some steps in common; for example, it may be desirable to process different liquid samples separately but detect all of the target analytes on the same portion of the device 10 and/or at the same time.

Figure 3:
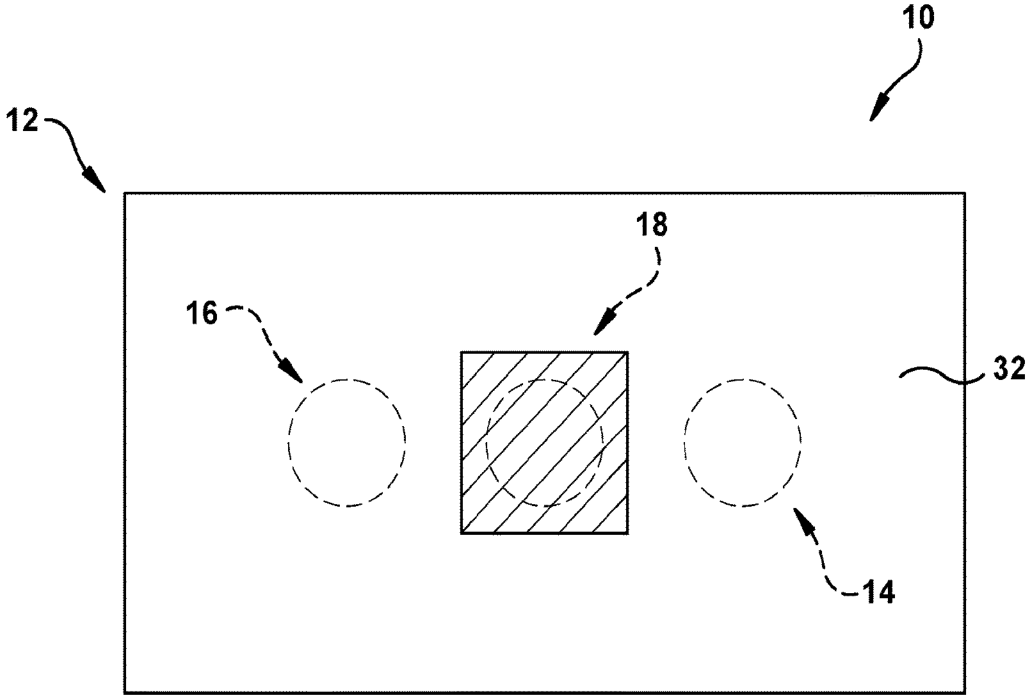
FIG. 3 is a schematic illustration showing a lower surface of the device in FIG. 1.
Figure 4:
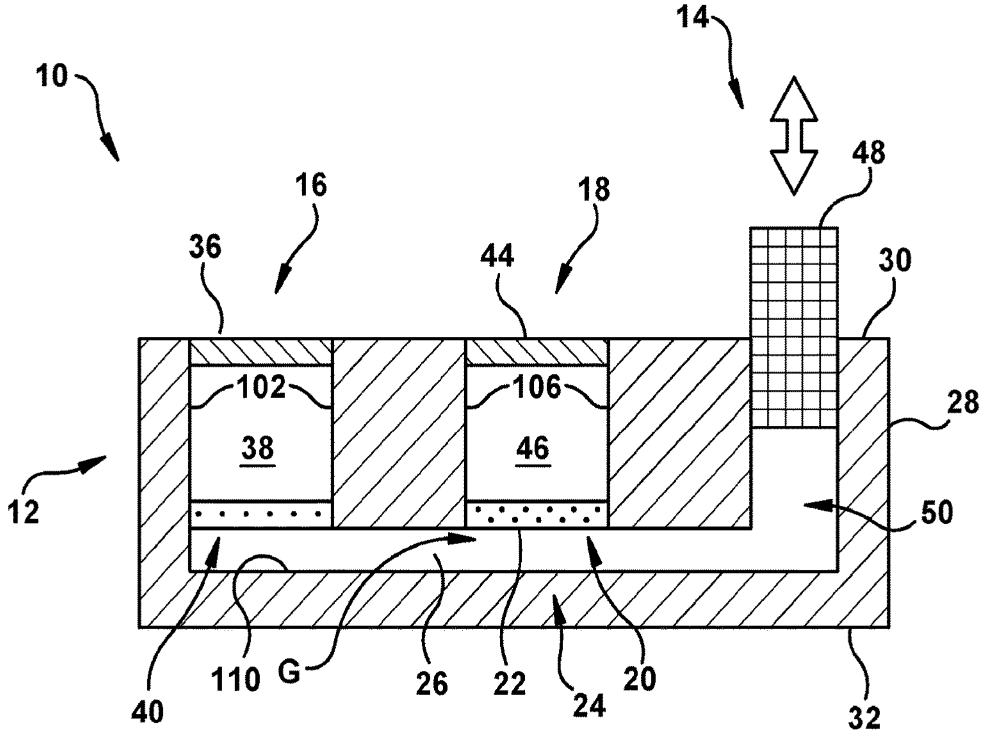
FIG. 4 is a schematic illustration showing a cross-sectional view taken along Line 4-4 in FIG. 1.

As shown in FIGS. 1-4, the housing 12 can have a rectangular shape and include a series of side walls 28 connected to oppositely disposed upper and lower surfaces 30 and 32. Although the housing 12 is depicted in FIGS. 1-4 as having a rectangular shape, it will be appreciated that the housing can have any desired shape (e.g., rectangular, puck-shaped, etc.). The dimensions (e.g., height, width, length) of the housing 12 can be varied as needed. All or only a portion of the housing 12 can be transparent. For example, all or only a portion of the lower surface 32 can be transparent. As shown in FIG. 3, for example, only a portion of the lower surface 32 adjacent the outlet 18 can be transparent. It will be appreciated that the housing 12 can include other components, such as a lid (not shown). In such instances, the lid can include one or more openings configured to overlay certain features of the housing 12, such as the inlet 16, the outlet 18, and the release mechanism 14. The lid can be releasably connected to the upper surface 30 of the housing 12 or, alternatively, securely bonded thereto.

Figure 7:
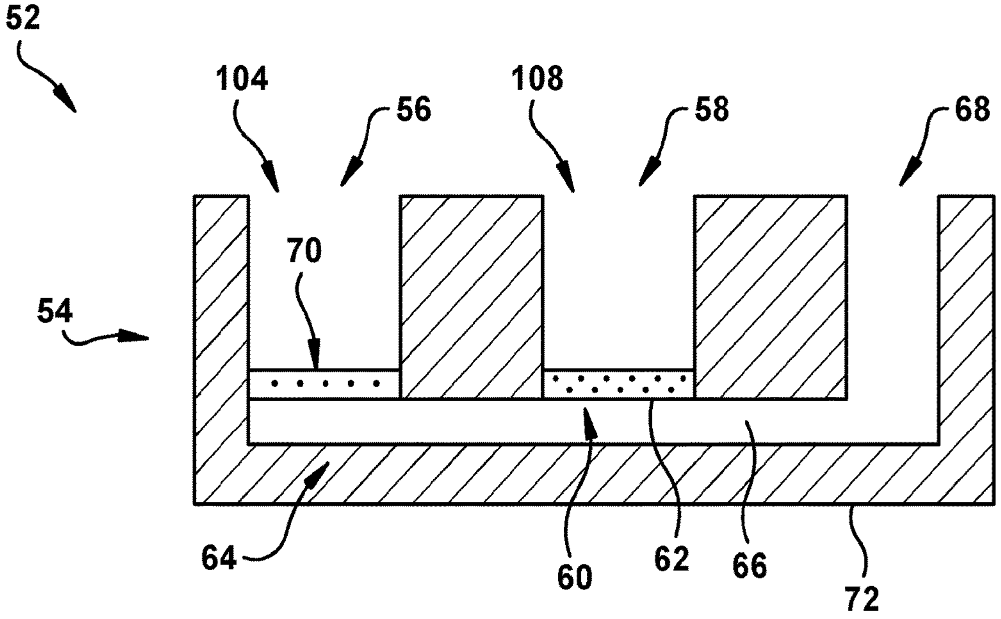
FIG. 7 is a schematic illustration showing a cross-sectional view taken along Line 7-7 in FIG. 6.

The inlet 16 (FIG. 4) of the housing 12 is sized and dimensioned to receive a liquid sample. The inlet 16 can be defined by one or more side walls 102 that define an interior 38 or lumen and an opening 104 (FIG. 7). In one example, the inlet 16 (FIG. 4) can include a single side wall 102 that defines a cylindrical interior 38 or lumen. The inlet 16 can be in fluid communication with the flow system 24 and include the opening 104 (FIG. 7) through which the liquid sample is deposited. The inlet 16 (FIG. 4) can have a circular cross-sectional profile; although, other cross-sectional profiles are possible depending upon the number and shape of the side walls 102. The inlet 16 can include a membrane or septum 36 that partitions the ambient environment from an interior 38 of the inlet and prevents unwanted material (e.g., dust) from entering the device 10. The inlet 16 can further include a filter 40 that is connected to the side wall(s) and partitions the interior 38 of the inlet from the channel 26 comprising the flow system 24. In some instances, pores comprising the filter 40 can have a size sufficient to permit passage of certain target analytes into the channel 26 while preventing passage of other larger particles. In one example, the pores of the filter 40 can have a size that permits a pathogen to pass into the channel 26 while preventing passage of larger cells (e.g., red blood cells) or cell debris.

The outlet 18 of the housing 12 is sized and dimensioned to permit removal of a volume of the liquid sample from the device 10. The outlet 18 can be spaced apart from the inlet 16 and be in fluid communication with the channel 26 of the flow system 24. The outlet 18 can be defined by one or more side walls 106 that define an interior 46 or lumen and an opening 108 (FIG. 7). In one example, the outlet 18 can include a single side wall 106 that defines a cylindrical interior 46 or lumen. The outlet 18 can have an opening 108 (FIG. 7) through which the liquid sample is partly or entirely removed. The outlet 18 (FIG. 4) can have a circular cross-sectional profile; although, other cross-sectional profiles are possible depending upon the number and shape of the side walls 106. The dimensions of the outlet 18 can be the same as or different than the dimensions of the inlet 16. The outlet 18 can include a vacuum gasket 44 that partitions the ambient environment from an interior 46 of the outlet. The vacuum gasket 44 permits a vacuum seal to be created within the outlet 18 while also preventing unwanted material (e.g., dust) from entering the device 10. The outlet 18 can further include a filter 20 that is connected to the side wall(s) and partitions the interior 46 of the outlet from the channel 26 of the flow system 24. In some instances, pores of the filter 20 can have a size that is less than the pore size of the inlet filter 40. For example, the pores of the outlet filter 20 can have a size that prevents passage of a pathogen into the interior 46 of the outlet 18 while permitting passage of the liquid sample therethrough.

The flow system 24 of the device 10 can include one or more channels 26 in fluid communication with the inlet 16, the outlet 18, and/or the release mechanism 14. Each channel 26 can comprise any suitable path, passage, or duct through, over or along which materials (e.g., liquid, target analytes, and/or reagents) may pass through the device 10. Each channel 26 may have any suitable dimensions and geometry, including width, height, length, and/or cross-sectional profile, among others, and may follow any suitable path, including linear, circular, and/or curvilinear, among others. Each channel 26 also may have any suitable surface contour, including recesses, protrusions, and/or apertures, and may have any suitable surface chemistry or permeability at any appropriate position within the channel. Each channel 26 may branch, join, and/or dead-end to form any suitable network. Accordingly, a channel 26 may function in target analyte positioning, sorting, retention, treatment, detection, propagation, storage, mixing and/or release, among others.

In one example, a diameter of each channel 26 can be less than about 100-90 microns, about 90-80 microns, about 80-70 microns, about 70-60 microns, about 60-50 microns, about 50-40 microns, about 40-30 microns, about 30-20 microns, about 20-10 microns, or about 10-5 microns, e.g., less than about 50 microns. The diameter of each channel 26 can be uniform across its length or may vary at one or more locations. In another example, a portion of the channel 26, indicated as a gap G, extending between a lower surface of the outlet filter 20 and a lower surface of the channel 26 can have a diameter of about 100-90 microns, about 90-80 microns, about 80-70 microns, about 70-60 microns, about 60-50 microns, about 50-40 microns, about 40-30 microns, about 30-20 microns, about 20-10 microns, or about 10-5 microns, e.g., less than about 50 microns to minimize the amount of unreacted detection reagent available to create background interference during detection. Moreover, the diameter of the channel 26 can be shaped and designed to reduce the volume of unbound or unreacted detection reagent(s) probed by a detector.

Advantageously, each channel 26 comprising the flow system 24 is sized and dimensioned to minimize the amount of unreacted detection reagent available to create background interference during detection, thereby improving the sensitivity of the device 10. This advantage is readily apparent considering conventional techniques used to reduced background when the detection signal is fixed. Confocal microscopy, for example, involves raster scanning of a focused point and refocusing that point virtually through a pinhole to remove background, and total internal reflection microscopy (or TIRF) focuses a laser at a critical angle onto a glass coverslip to create a very thin (e.g., 100 nm) layer of light. Additionally, nanoscale chambers are fashioned out of a flexible polymer, which is then placed over a single molecule of interest and sealed. Confocal microscopy and TIRF fall under the class of "optical sectioning", whereby the background is removed by using optics to probe only a thin area of interest. Fashioning nanoscale chambers out of a flexible polymer employs geometry, but with a flexible or deformable chamber that is adapted to the random positions of the analyte. The channel 26 of the present disclosure, conversely, provides a fixed geometry that advantageously reduces background while allowing sample preparation simultaneously without optical sectioning or deformable chambers.

In another aspect, all or only a portion of the flow system 24 can be coated with one or more detection reagents. The detection reagents can be the same or different. In one example, all or only a portion of the wall(s) 102 defining the inlet 16 can be coated with one or more detection reagents. In another example, all or only a portion of the wall(s) 106 defining the outlet 18 can be coated with one or more detection reagents. In another example, all or only a portion of the wall(s) 110 defining the channel 26 can be coated with one or more detection reagents. In another example, only a portion of the channel 26 which is subject to light (e.g., from a photodetector) is coated with one or more detection reagents.

In some instances, a detection reagent may be combined with a slow-release compound or polymer (e.g., poly(lactic-co-glycolic acid)). In such instances, the resultant slow-release detection reagent can be flowed through the flow system 24 and then lyophilized to coat all or only a portion thereof. Other methods of coating can include spin-coating with drying and/or aerosolization processes. Thus, it will be appreciated that coating may be applied to certain components or features of the device 10 prior to assembly, e.g., so only certain parts of the flow system 24 are coated.

In other instances, the inlet filter 40 can be coated with a slow-release detection reagent (as described above). The slow-release detection reagent may be attached to the inlet filter 40 as described above or, alternatively, the detection reagent may be integrated into beads made of a slow-release compound or polymer (e.g., poly(lactic-co-glycolic acid), which are placed onto the inlet filter. As a liquid sample is flowed through the inlet 16, the beads can dissolve and thereby release the detection reagent into the liquid sample.

Coating one or more portions of the device 10 with one or more detection reagents provides several advantages. First, very high concentrations of detection reagent(s) can be obtained for the same amount of detection reagent(s) (as opposed to directly mixing the detection agent(s) with the liquid sample) because the volume of the flow system 24 is very small. Such high concentrations can improve the limit of detection. And, second, the fact that the detection reagent(s) is/are coated onto the device 10, as opposed to adding the detection reagent(s) with the liquid sample, creates a "single-step" process whereby only the liquid sample needs to be added to the device. In addition to improved user convenience, this reduces user-induced variation and error, which are the largest sources of diagnostic uncertainty.

In another aspect, the device 10 can additionally or optionally include a release mechanism 14 that is coupled to the housing 12 and in fluid communication with each channel 26 comprising the flow system 24. Advantageously, the release mechanism 14 is configured to permit selective release of a retained target analyte off of the surface 22 of the outlet filter 20. Release of the retained target analyte from the surface 22 of the outlet filter 20, which can be source of background interference during detection, minimizes interference (e.g., autofluorescence) and improves sensitivity of the device 10 by moving the retained target analyte to an area of relatively low background interference. The release mechanism 14 can generally comprise any one or combination of structures, components, or elements that enable movement of a retained target analyte away from a preselected site/area (e.g., the outlet filter 20) by removing, overcoming, and/or rendering ineffective the force(s) that retains the target analyte. After release, the target analyte may have any suitable destination within the flow system 24 that improves target analyte detection.

Figure 5:
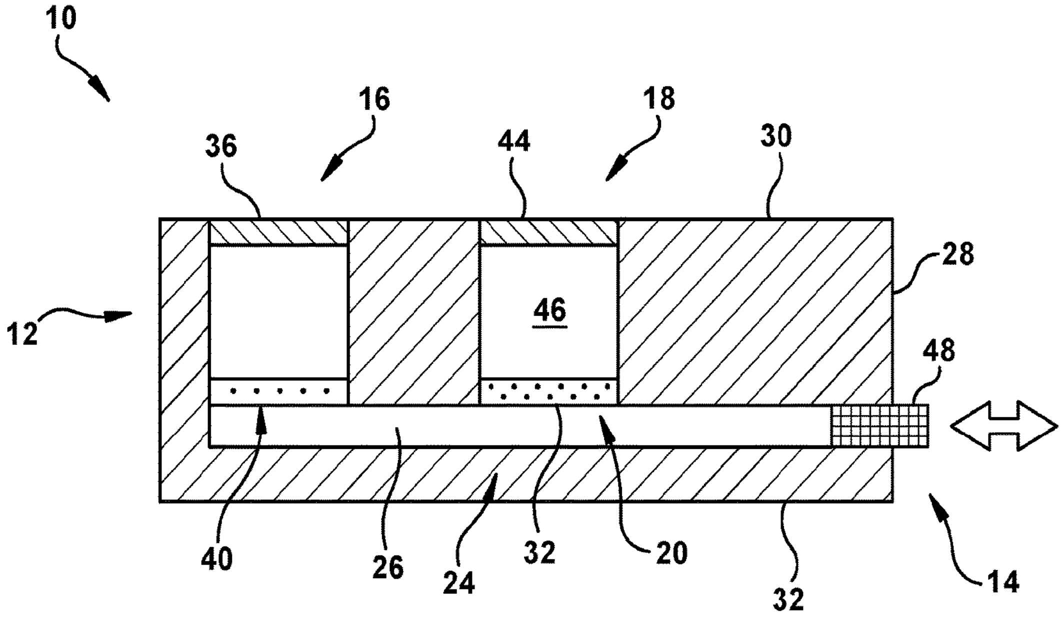
FIG. 5 is a schematic illustration showing an alternative configuration of the device in FIG. 4.

The structures, components, or elements of the release mechanism 14 can be configured for precise control of the retained target analyte within the flow system 24. Such structures, elements, or components may be controllable by tactile, electronic and/or robotic means, and may be connected (e.g., directly connected) to the housing 12. In one example, the release mechanism 14 can comprise a plug member 48 that is slidably disposed within a second outlet 50 of the housing 12. When disposed in the second outlet 50, the plug member 48 provides a retaining force on flow of the liquid sample through the flow system 24. The position of the liquid sample within the flow system 24 can be precisely controlled by manipulating the plug member 48 within the second outlet 50. By moving the plug member 48 axially away from the housing 12, for example, the liquid sample can flow through the channel 26 towards the release mechanism 14 and thereby move the retained target analyte off of the outlet filter 20. In one example, the plug member 48 can comprise a set screw. It will be appreciated that the release mechanism 14 can have other configurations, such as the one shown in FIG. 5.

In another example, the release mechanism 14 can include a syringe (not shown) that is capable of being fluidly coupled to the outlet 18 or the second outlet 50 of the device 10.

In instances where the device 10 does not include a release mechanism 14, it will be appreciated that suction or a vacuum (e.g., from a syringe) can be selectively applied (e.g., fluidly coupled) to the second outlet 50 to move the retained target analyte off of the outlet filter 20.

It will also be appreciated that the device 10 can include other features to facilitate ease of use and improve target analyte detection. For example, the device 10 can include one or more fluid reservoirs (not shown), such as a suitable receptacle or chamber for storing materials (e.g., reagents) before, during, between, and/or after target analyte detection. Such reservoirs may include input, intermediate, and/or output reservoirs. Input reservoirs may store materials prior to inputting the liquid sample into the device 10. By contrast, intermediate reservoirs may store materials during and/or between uses of the device 10. Finally, output reservoirs may store materials prior to outputting from the device 10, for example, to an external processor or waste, or prior to disposal of the device. Additionally, reagents may be dried onto the wall(s) defining each of the channel 26, the inlet 16, the outlet 18 and/or the second outlet 50.

Figure 6:
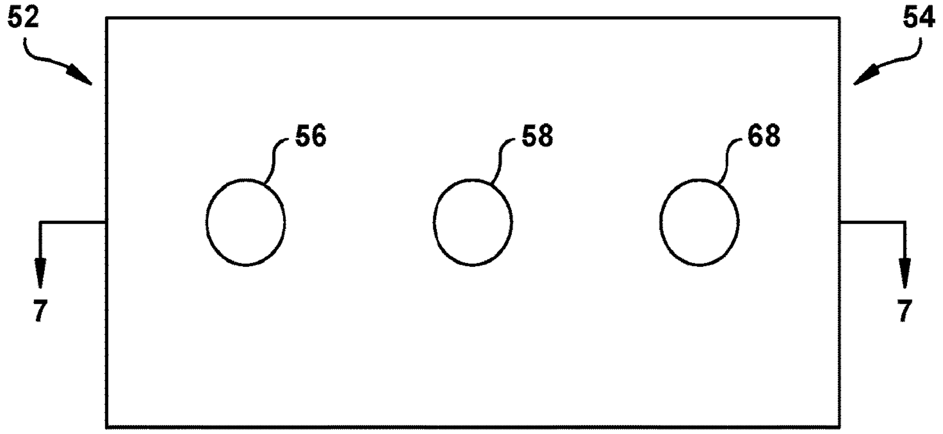
FIG. 6 is a schematic illustration showing an upper surface of a device for detecting a target analyte in a liquid sample constructed in accordance with another aspect of the present disclosure.

FIGS. 6-7 illustrate a device 52 for detecting a target analyte in a liquid sample constructed in accordance with another aspect of the present disclosure. Except where described below, the device 52 can be identically constructed as the device 10 shown in FIGS. 1-4. For example, the device 52 can comprise a housing 54 that includes an inlet 56 for receiving a liquid sample, an outlet 58 for removing a volume of the liquid sample from the device, a filter 60 associated with the outlet and being sized and dimensioned to retain a target analyte on a surface 62 thereof, and a flow system 64 comprising at least one channel 66 that is in fluid communication with the inlet, the outlet, and a second outlet 68. As described for the device 10 above, the device 52 can include an inlet filter 70 and an outlet filter 60 disposed in the inlet 56 and the outlet 58, respectively. The device 52 can additionally or optionally include a septum (not shown) and a vacuum gasket (not shown) (as described above).

In use, a liquid sample can be loaded into the inlet 56 of the device 52. The liquid sample can be pre-processed (e.g., centrifuged) prior to loading into the inlet 56. Pressure can then be applied (e.g., by applying an additional fluid into the inlet 56) to force the liquid sample through the inlet filter 70 into the channel 66. Larger particles (e.g., red blood cells) can be captured by the inlet filter 70. The liquid sample can then move through the channel 66 and be pulled into the outlet 58 via a suction or vacuum force, which is applied to the outlet. As the liquid sample moves into the outlet 58, pathogens are trapped on the surface 62 of the outlet filter 60. Any red blood cells, for example, captured on the surface 62 of the outlet filter 60 can be lysed by administering a lysing solution into the second outlet 68. The lysed cells can then be removed through the outlet 58.

Next, a detection reagent specific for a target analyte can be loaded into the inlet 56 and flowed through the channel 66 until it contacts the target analyte, if present, retained on the surface 62 of the outlet filter 60. The detection reagent can react with the target analyte directly, or react with a biomolecule associated therewith, and thereby provide a detectable signal (e.g., fluorescence). For direct-binding detection reagents, excess/unbound probe can be washed off after this step. The unbound or unreacted detection reagent may reside between the outlet filter 60 and the bottom of the channel 66 and thus provide a source of background interference during detection. To reduce background interference, the outlet filter 60 can be depressed towards the lower surface 72 of the housing 54 to displace any unbound or unreacted detection reagent. A photodetector (not shown) can then be used to detect the presence of the target analyte. The detected signal can be subsequently analyzed to provide information about the target analyte (e.g., quantity).

It will be appreciated that the order of steps involved in operation of the device 52 may be changed, or that certain steps may be omitted depending upon the particular application. For example, the liquid sample could be filtered to remove certain particles (e.g., red blood cells) prior to loading into the inlet 56. Alternatively, a lysing solution could be added to the liquid sample before loading into the inlet 56.

Figure 8A:
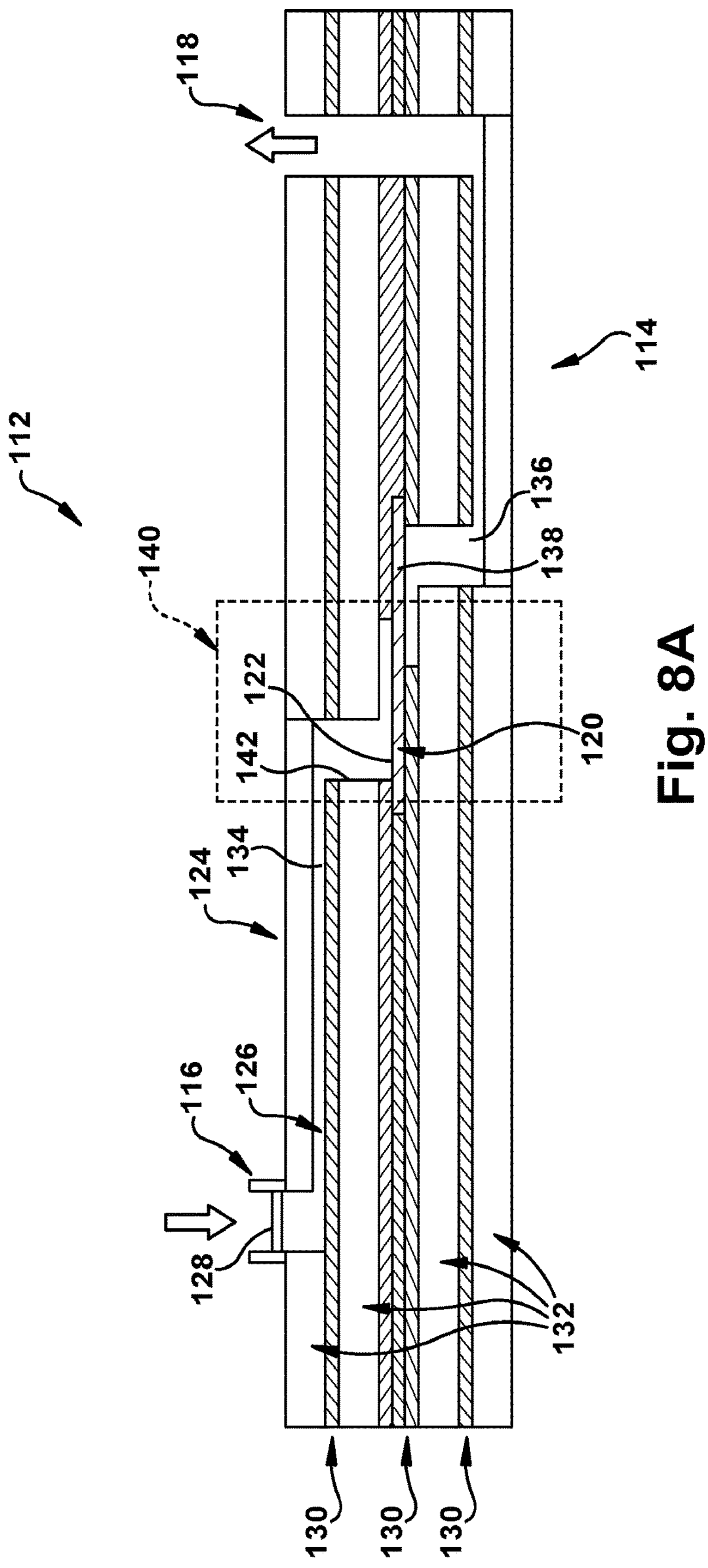
FIGS. 8A-C are a series of schematic illustrations showing an alternative configuration of the device in FIGS. 1-4.
Figure 8B:
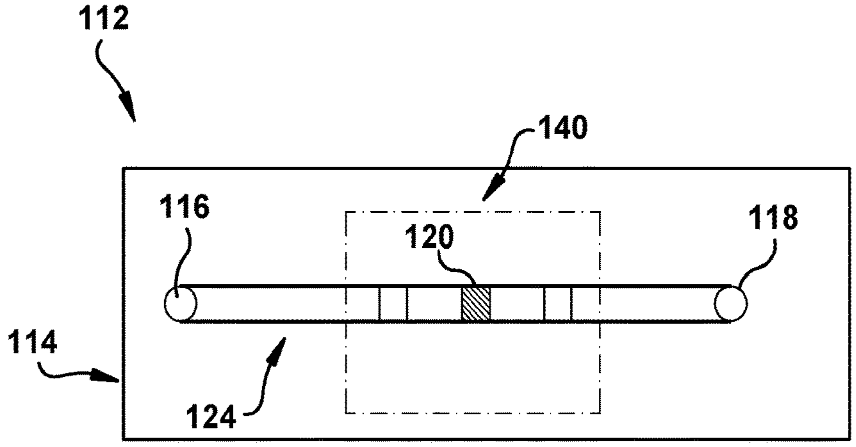
Figure 8C:
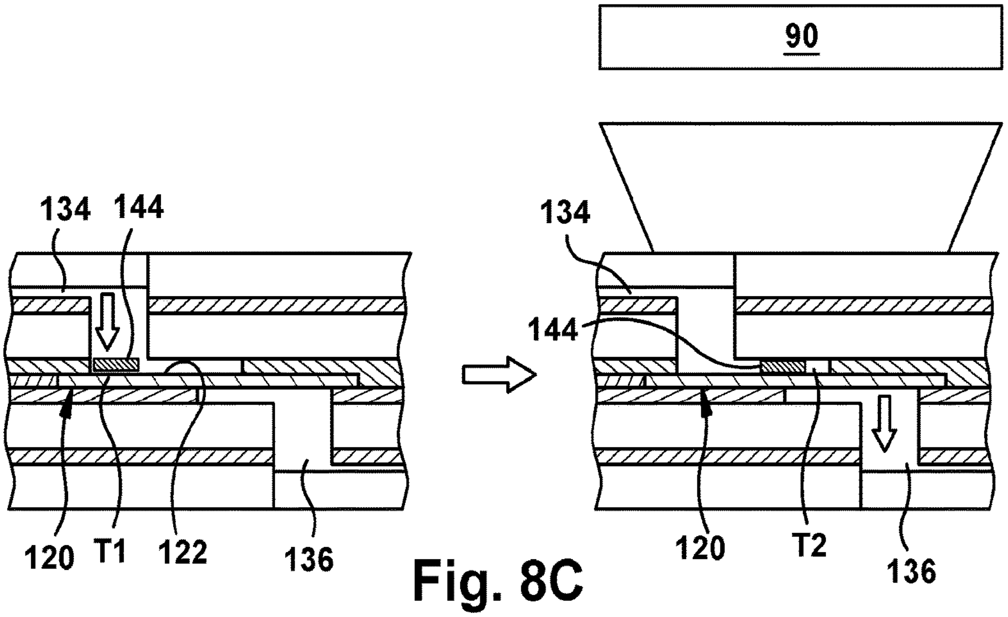

FIGS. 8A-C illustrate a device 112 for detecting a target analyte in a liquid sample constructed in accordance with another aspect of the present disclosure. Except where described below, the device 112 can be identically constructed as the devices 10 and 52 shown in FIGS. 1-7. For example, the device 112 can comprise a housing 114 that includes an inlet 116 for receiving a liquid sample, an outlet 118 for removing a volume of the liquid sample from the device, a filter 120 sized and dimensioned to retain a target analyte on a first surface 122 thereof, and a flow system 124 comprising at least one channel 126 that is in fluid communication with the inlet and the outlet. As described for the devices 10 and 52 above, the device 112 can include an inlet filter 128 disposed in the inlet 116. It will be appreciated that the device 112 can additionally or optionally include a septum (not shown) and a vacuum gasket (not shown) (as described above).

Referring to FIG. 8A, the device 112 can have a multilayer configuration comprising multiple double-sided adhesive layers 130 disposed between multiple acrylic or plastic layers 132 (e.g., plates). The filter 120 is centrally located within the device 112, e.g., disposed between adjacent double-sided adhesive layers 130. The filter 120 partitions the flow system 124 such that a first channel 134 extends between the inlet 116 and the first surface 122 of the filter, and a second channel 136 extends between a second surface 138 of the filter and the outlet. Advantageously, the multilayer configuration permits use of a thicker filter 120 (as compared to the filter described above) and increased flow rates throughout the device 112. For example, the multilayer configuration permits the use of a coated filter 120 (e.g., with Irgalan Black or other sputter metal film) or an aluminum oxide filter, which allows high flow rates and precise control over pore geometry, both of which function to decrease autofluorescence.

In some instances, all or only a portion of the first channel 134 can be coated with one or more detection reagents. In one example, an imaging region 140 (indicated by dashed lines) of the first channel 134 is coated with one or more detection reagents. In this example, the wall or walls 142 defining the imaging region are coated with the detection agent(s). Advantageously, coating the imaging region 140 with one or more detection agents removes the need to flow the detection reagent(s) through the device 112 for detection of the target analyte.

In use, a liquid sample can be loaded into the inlet 116 of the device 112. The liquid sample can be pre-processed (e.g., centrifuged) prior to loading into the inlet 116. Pressure can then be applied (e.g., by applying an additional fluid into the inlet 116) to force the liquid sample through the inlet filter 128 into the first channel 134. Larger particles (e.g., red blood cells) can be captured by the inlet filter 128. The liquid sample can then move through the first channel 134 and be pulled into contact with the first surface 122 of the filter 120 via a suction or vacuum force, which is applied to the outlet 118. As the liquid sample moves through the filter 120, pathogens are trapped on the first surface 122.

Next, a detection reagent specific for a target analyte can be loaded into the inlet 116 and flowed through the first channel 134 until it contacts the target analyte, if present, retained on the first surface 122 of the filter 120. Accumulation of the target analyte effectively concentrates the target analyte, thereby removing the need to separately concentrate the analyte (e.g., by culturing) in a separate instrument or device. In some instances, the target analyte (bound to the detection reagent) can accumulate on the first surface 122 of the filter 120 and form a substantially continuous layer 144 (FIG. 8C) thereon.

The detection reagent can react with the target analyte directly, or react with a biomolecule associated therewith, and thereby provide a detectable signal (e.g., fluorescence). After a desired period of time, a release mechanism (not shown) can be actuated. For example, a syringe can be used to remove some of the liquid sample from the outlet 118. Actuation of the release mechanism causes the liquid sample to move from a first threshold T1 to a second threshold T2 (FIG. 8C). As the liquid sample flows to the second threshold T2, the target analyte (bound to the detection reagent) retained on the first surface 122 of the filter 120 is displaced off of the filter to a location suitable for detection of the target analyte. A photodetector (not shown) can then be used to detect the presence of the target analyte. The detected signal can be subsequently analyzed to provide information about the target analyte (e.g., quantity).

It will be appreciated that the order of steps involved in operation of the device 112 may be changed, or that certain steps may be omitted depending upon the particular application. For example, the liquid sample could be filtered to remove certain particles (e.g., red blood cells) prior to loading into the inlet 116. Alternatively, a lysing solution could be added to the liquid sample before loading into the inlet 56.

Figure 9A:
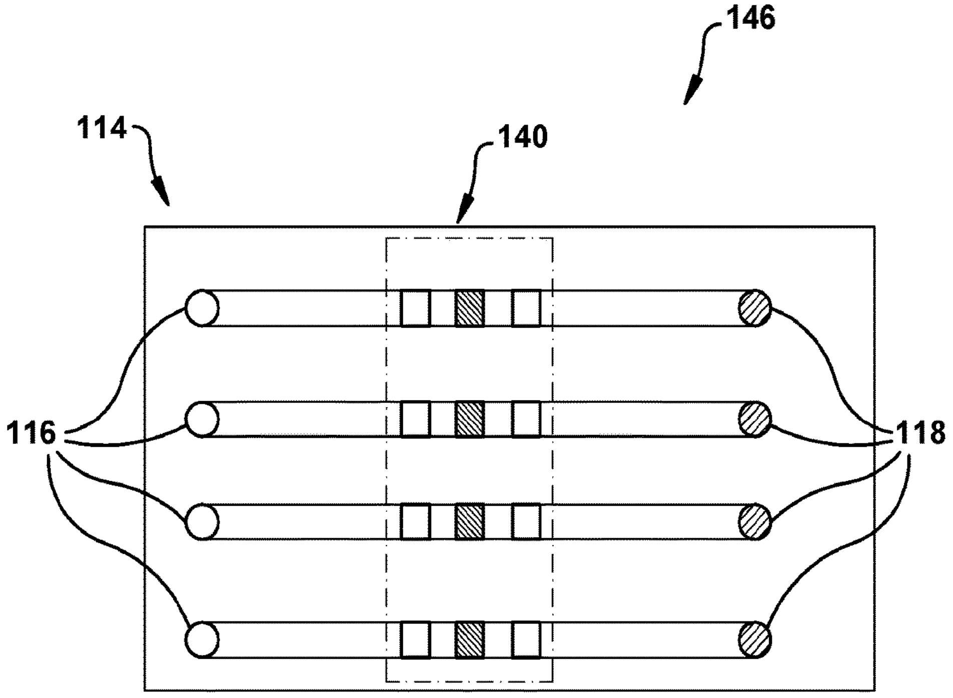
FIGS. 9A-B are schematic illustrations showing the device in FIGS. 8A-C configured as a multi-channel device, such as a 4-channel device (FIG. 9A) and a 2-channel device (FIG. 9B)
Figure 9B:
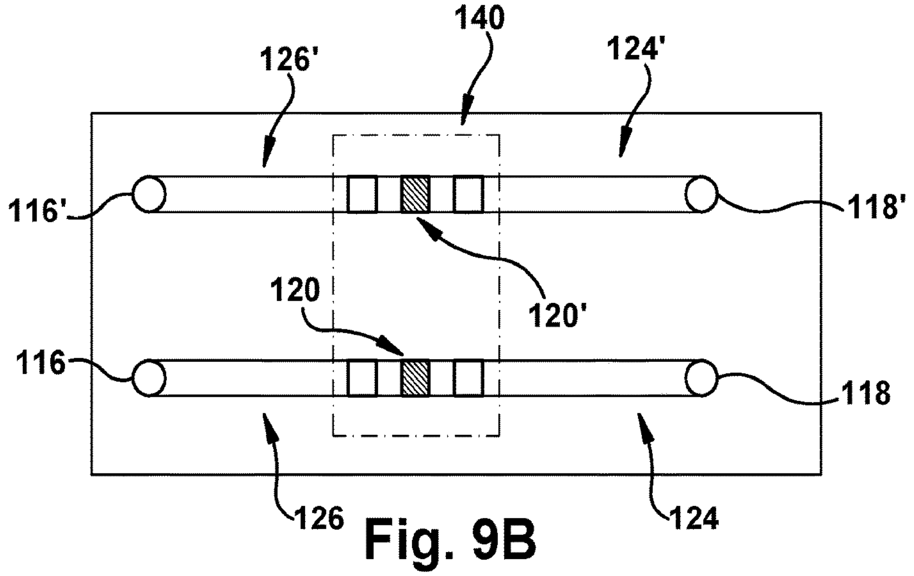

In some instances, the device 112 shown in FIGS. 8A-C can be configured as a multi-channel device 146 (FIG. 9A). Each "channel" can comprise the features or components of the device 112 shown in FIGS. 8A-C and described above, including the inlet 116, the outlet 118, the filter 120, and the flow system 124. Thus, in one example, a multi-channel device 146, e.g., a two-channel device 146' (FIG. 9B) can include a second "channel" that is arranged in parallel to the other "channel" and comprises the following features: a second inlet 116' for receiving a second liquid sample; a second outlet 118' for removing a volume of the second liquid sample from the device; a second filter 120' associated with the second outlet and being sized and dimensioned to retain a target analyte on a surface thereof; and a second flow system 124' comprising at least one channel 126' that is in communication with the second inlet and the second outlet.

Having multiple "channels" advantageously allows simultaneous testing of many liquid samples and/or the ability to probe multiple target analytes in a single liquid sample. In one example, a multi-channel device 146 can include four "channels"; however, it will be appreciated that the device can include any number of "channels" (e.g., two, three, five, or more). Each "channel" of the multi-channel device 146 can be in close proximity to the other channel(s). For example, each "channel" of the device 146 can be spaced apart from the other "channel(s)" by a distance of about 5 mm to about 4 mm, about 4 mm to about 3 mm, about 3 mm to about 2 mm, about 2 mm to about 1 mm, about 1 mm to about 0.5 mm, or about 0.5 mm to about 0.1 mm. In one example, each "channel" of the device 146 can be spaced apart from the other "channel(s)" by a distance of 0.2 mm. The close proximity of the "channels" relative to one another advantageously minimizes spatial variation in temperature, excitation intensity, and emission collection optics (e.g., numerical aperture).

Figure 10:
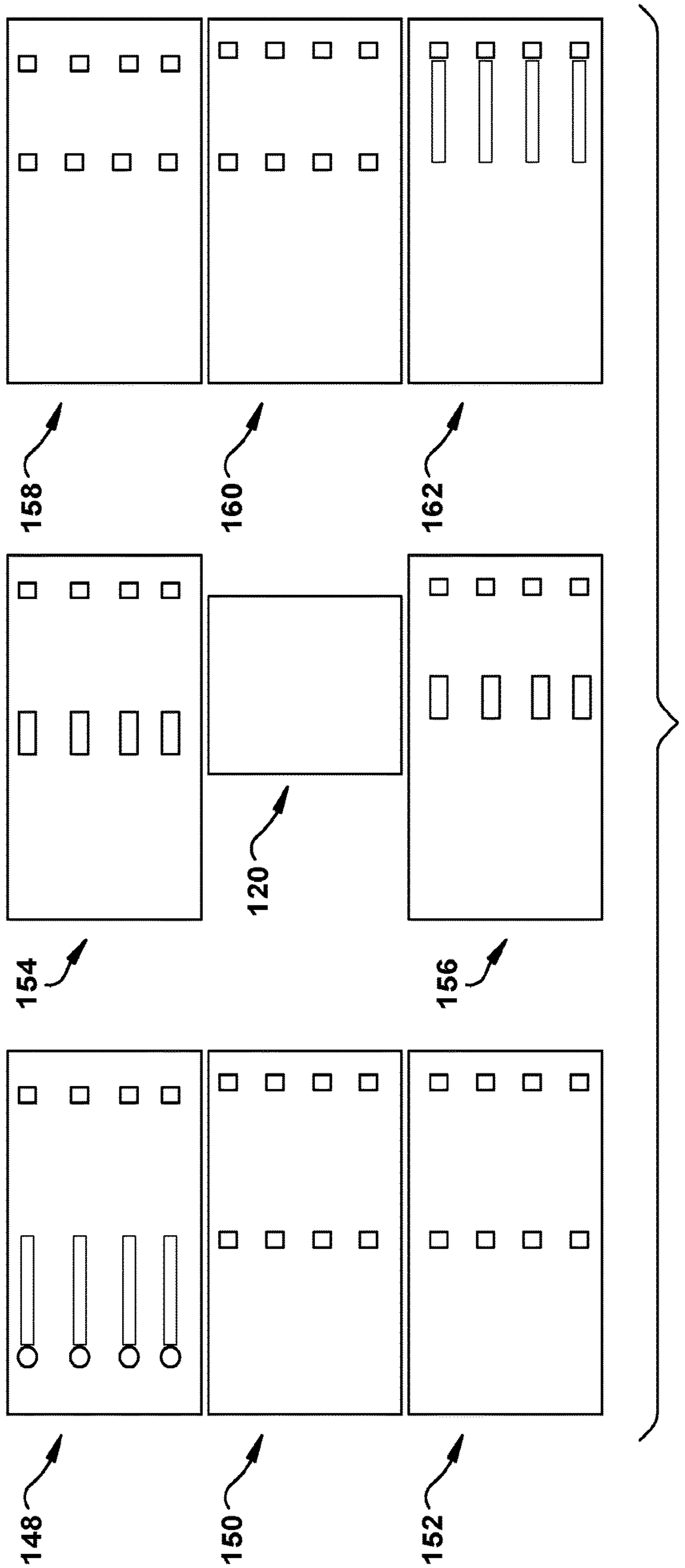
FIG. 10 is a schematic illustration showing an exploded view of the multi-channel device in FIG. 9.

An exploded view of the 4-channel device 146 is shown in illustrated in FIG. 10. The 4-channel device 146 can comprise the following layers: a first acrylic layer 148 that forms the top of the device; a second layer 150 comprising a double-sided adhesive; a third acrylic layer 152; a fourth layer 154 comprising a double-sided adhesive; a fifth layer 120, i.e., the filter; a sixth layer 156 comprising a double-sided adhesive; a seventh acrylic layer 158; an eighth layer 160 comprising a double-sided adhesive; and a ninth acrylic layer 162 that forms the bottom of the device. Manufacture of each layer 148-162 can be precisely controlled using known MEMS techniques, for example. During assembly of the device 146, inlet adaptors (e.g., rubber septa for needles, barbed fittings for tubing, Leur lock connectors, any pre-filtration) (not shown) can be applied to each inlet 116 to prevent clogging of the flow system 124 (e.g., the first channel 134) with adhesive. Also during assembly, individual acrylic layers 132 can be sealed firmly with double-sided adhesive 130 before bonding the acrylic layers to one another or to the filter 120.

Methods

Figure 11:
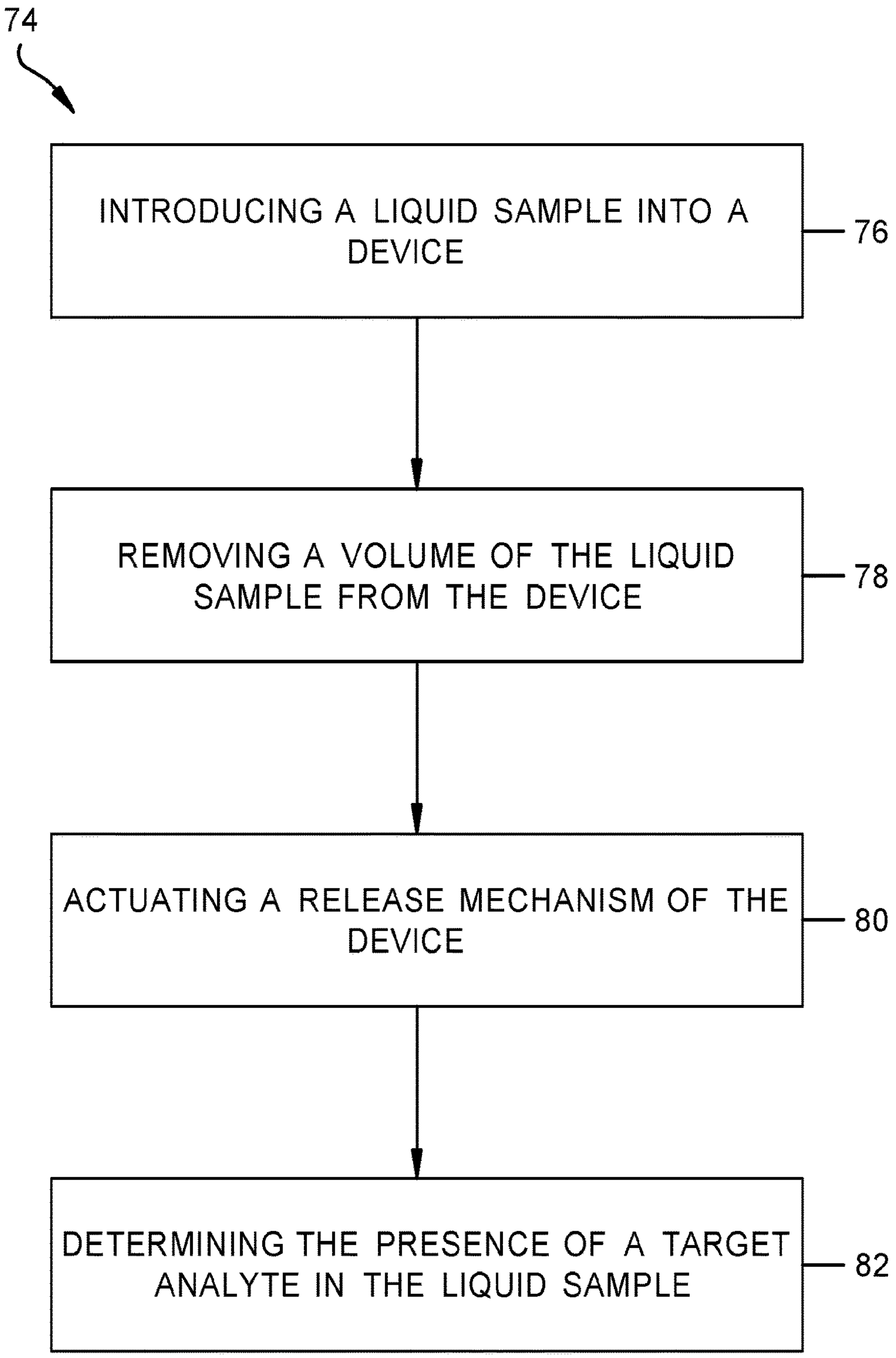
FIG. 11 is a process flow diagram illustrating a method for detecting a target analyte in a liquid sample according to another aspect of the present disclosure.

Another aspect of the present disclosure can include a method 74 (FIG. 11) for detecting a target analyte in a liquid sample. In one example, the method 74 can be performed using the device 10 illustrated in FIGS. 1-4 and described above. Generally, the method 84 can include the steps of: introducing, through the inlet 16 of the device 10, a liquid sample either before, during, or after introduction of a detection reagent through the inlet (Step 76); removing, from an outlet 18 of the device, a volume of the liquid sample to cause a target analyte, if present, to be retained on a surface 22 of the filter associated with the outlet (Step 78); actuating the release mechanism 14 of the device to cause release of the retained target analyte of off the surface of the outlet filter (Step 80); and determining the presence of the target analyte in the liquid sample. The method 74 can find use in a variety of settings and with a number of applications, such as use in a point-of-care environment or for high-throughput analysis. For example, operation of the device 10 can be accomplished or assisted using an automated machine (not shown), such as the VITEK 2 system (bioMérieux, Durham, N.C.) or the BD PHOENIX Automated Microbiology System (Becton Dickson, Inc., Franklin Lakes, N.J.).

Figure 12:
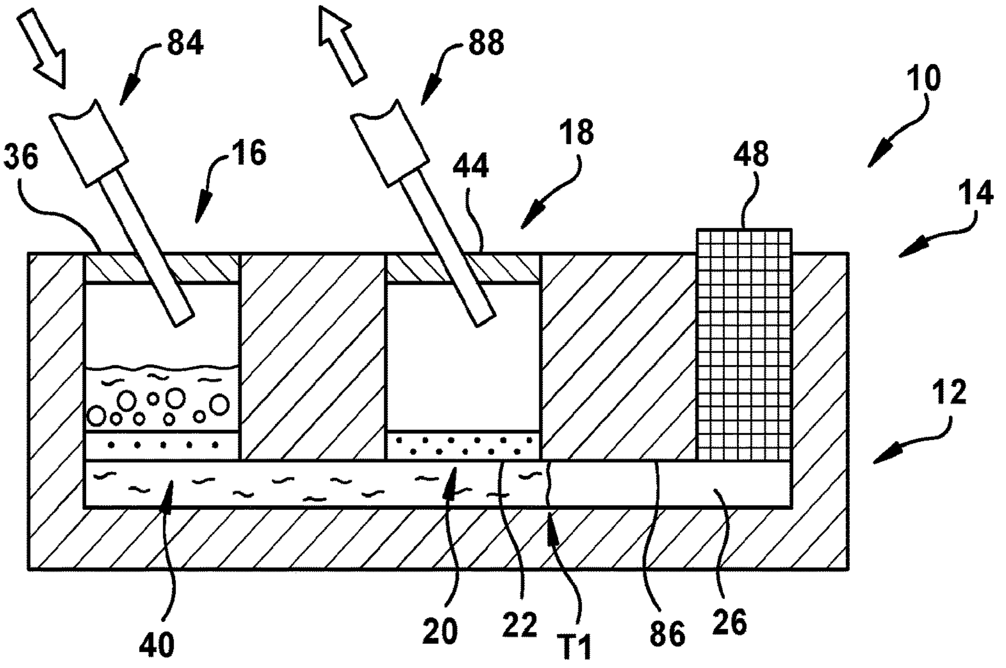
FIG. 12 is a cross-sectional view of the device in FIGS. 1-4 showing a liquid sample being injected into an inlet of the device.

At Step 76 of the method 74, a liquid sample can be loaded into the inlet 16 of the device 19 before, during, or after introduction of a detection reagent (FIG. 12). The liquid sample can be previously withdrawn from a subject using a hypodermic needle 84, for example, and then loaded directly into the inlet 16 by inserting the needle through the septum 36 and dispensing the liquid sample into the interior 38 of the inlet. Alternatively, the liquid sample can be pre-processed (e.g., centrifuged, contacted with one or more reagents, etc.) prior to loading into the inlet 16. Depending upon the manner in which the liquid is pre-processed, the inlet filter 40 may not be present in the device 10. For example, the inlet filter 40 may not be needed where the liquid sample is pre-processed with a red blood cell lysing solution.

Before the liquid sample is loaded into the inlet 16, the plug member 48 comprising the release mechanism 14 can be situated in a first position (as shown in FIG. 12). Any one or combination of forces (e.g., mechanical, tactile, electrical, etc.) can be used to situate the plug member 48 in the first position. In the first position, a retention force is applied to the liquid sample to create a first threshold T1. The first threshold is located within the channel 26 such that the liquid sample contacts substantially the entire surface 22 of the outlet filter 20, but not an upper surface 86 of the channel 26 adjacent the outlet filter.

With the liquid sample loaded into the inlet 16, the liquid sample can be flowed into the channel 26 through the inlet filter 40 and into the outlet 18 by applying suction or vacuum to the outlet. Application of a vacuum can be done by inserting a suction device 88 through the vacuum gasket 44 into the interior 46 of the outlet 18. The vacuum can be established by a mechanical or physical action, which creates the vacuum substantially simultaneously with the introduction or movement of the liquid sample. The mechanical or physical action can be associated with a peristaltic pump, a piston pump, a membrane pump, a centrifugal pump, or a syringe. Suction can be applied to the suction device 88 to remove a volume of the liquid sample (Step 78). As the liquid sample is flowed through the channel 26, certain particles (e.g., red blood cells) can be captured by the inlet filter 40 and prevented from entering the channel 26 while the target analyte, if present, can pass into the channel.

Figure 13:
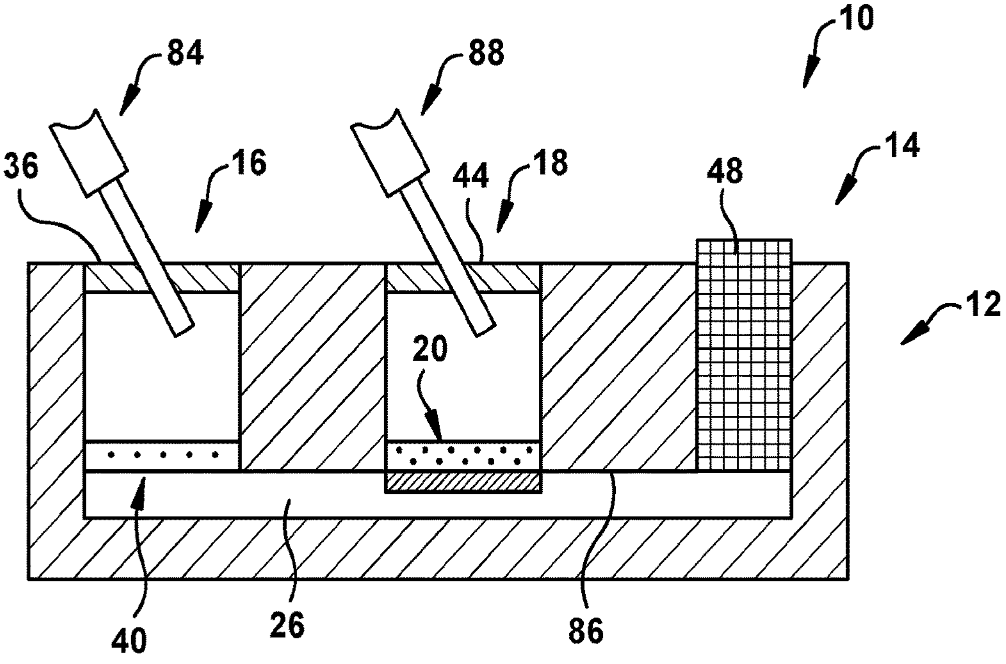
FIG. 13 is a cross-sectional view of the device in FIG. 12 showing a target analyte (solid rectangle) retained on a filter of the device.

At Step 78, all, or substantially all, of the liquid sample can be drawn through the outlet 18 and removed by the suction device 88. As the liquid sample is withdrawn from the device 10, the target analyte, if present, can accumulate on the surface 22 of the outlet filter 20 (FIG. 13). Accumulation of the target analyte effectively concentrates the target analyte, thereby removing the need to separately concentrate the analyte (e.g., by culturing) in a separate device or instrument. In some instances, the target analyte can accumulate on the surface 22 of the outlet filter 20 and form a substantially continuous layer thereon.

Figure 14:
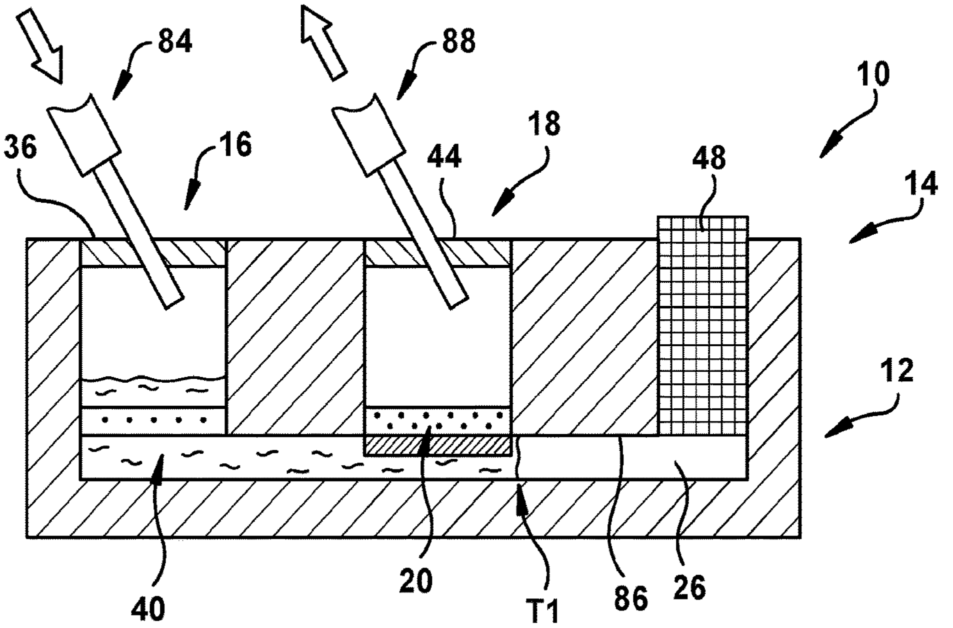
FIG. 14 is a cross-sectional view of the device in FIG. 13 showing a detection reagent being injected into the inlet of the device.
Figure 15:
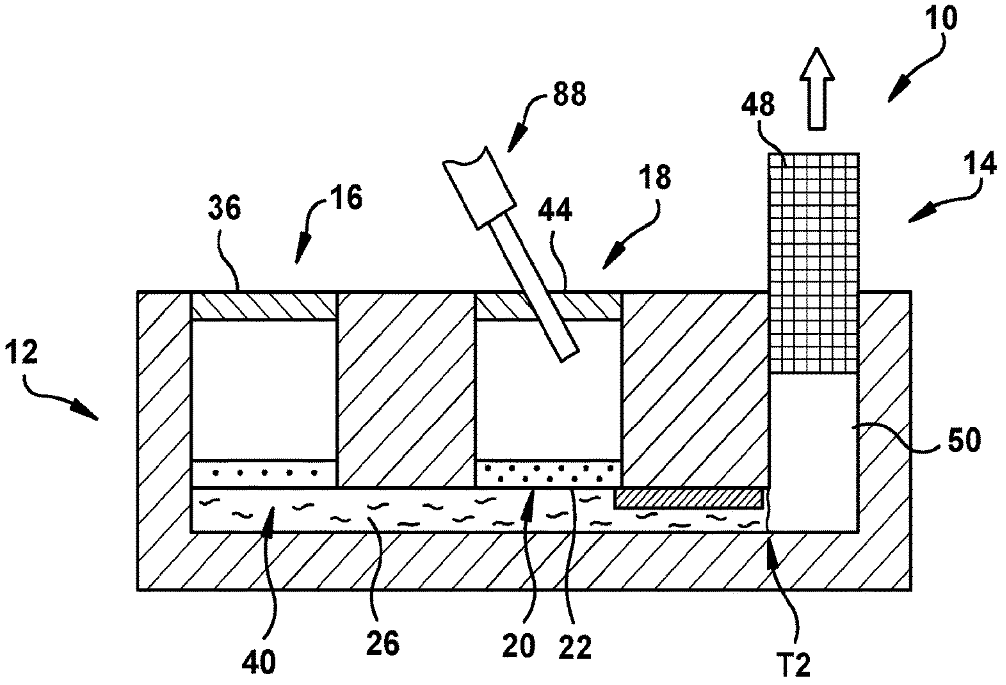
FIG. 15 is a cross-sectional view of the device in FIG. 14 showing the retained target analyte being released off of the filter upon actuation of a release mechanism associated with the device.

If it has not been done so already, a liquid containing detection reagent specific for a particular target analyte can be introduced into the device 10 (FIG. 14). The detection reagent can be added in an amount and for a time sufficient to enable binding between the target analyte, if present, and the detection reagent. After a desired period of time, the release mechanism 14 can be actuated at Step 80. As shown in FIG. 15, the release mechanism 14 can be actuated by moving the plug member 48 axially away from the housing 12 to a second position. Movement of the plug member 48 from the first position to the second position causes the liquid sample to move from the first threshold T1 to a second threshold T2. As the liquid sample flows to the second threshold T2, the target analyte retained on the surface 22 of the outlet filter 20 is displaced off of the outlet filter to a location suitable for detection of the target analyte.

Figure 16:
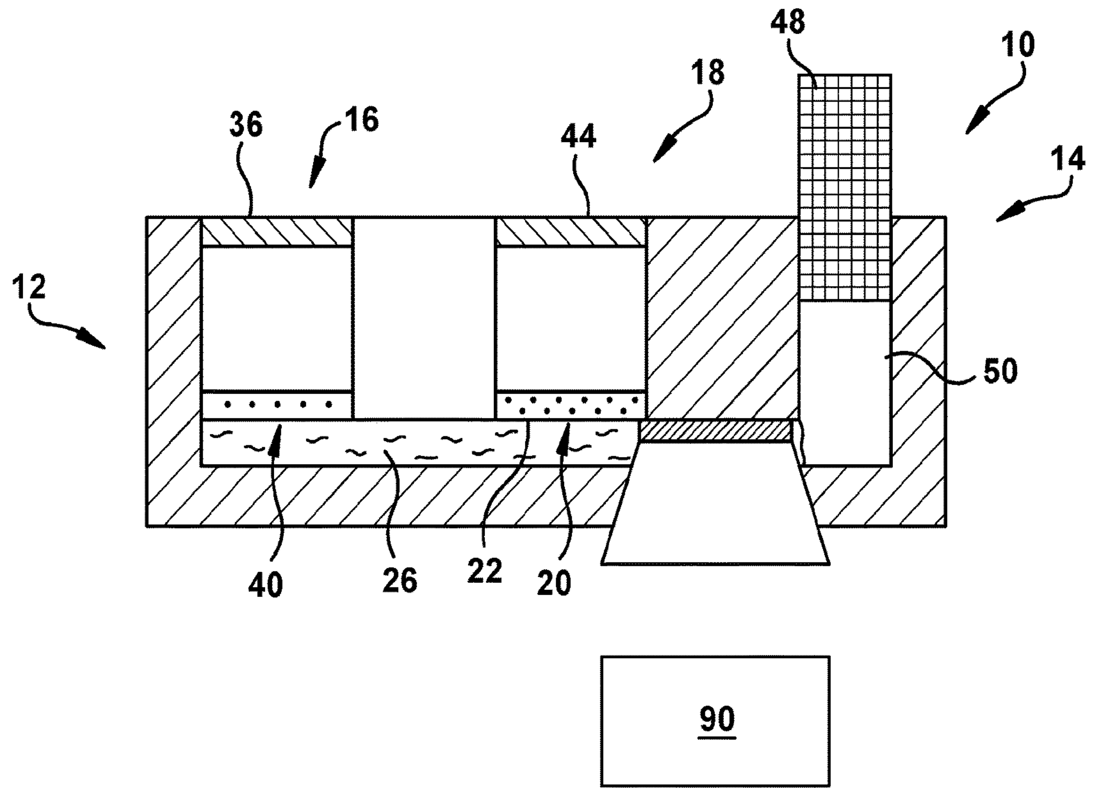
FIG. 16 is a cross-sectional view of the device in FIG. 15 showing detection of an emitted signal generated upon reaction of the detection reagent with a target analyte.

At Step 82, the presence of the target analyte in the liquid sample can be determined. A detector 90 (FIG. 16) can be used to detect the target analyte. Examples of detectors 90 can include any machine equipped with a spectrophotometer, fluorometer, luminometer, photomultiplier tube, photodiode, nephlometer, photon counter, electrodes, ammeter, voltmeter, capacitive sensors, radio-frequency transmitter, magnetoresistometer, or Hall-effect device. The detected signal can then be analyzed to provide information about the captured analyte (e.g., quantity or associated biomolecule activity characteristic(s)).

Advantageously, the method 74 permits highly sensitive target analyte detection by significantly reducing background interference during detection. The micron-sized channel 26, for example, improves sensitivity by reducing the volume of liquid containing unreacted detection reagent. Additionally, the release mechanism 14 improves sensitivity by displacing captured target analyte off of the outlet filter 20, which is a source of background interference during detection.

Figure 17:
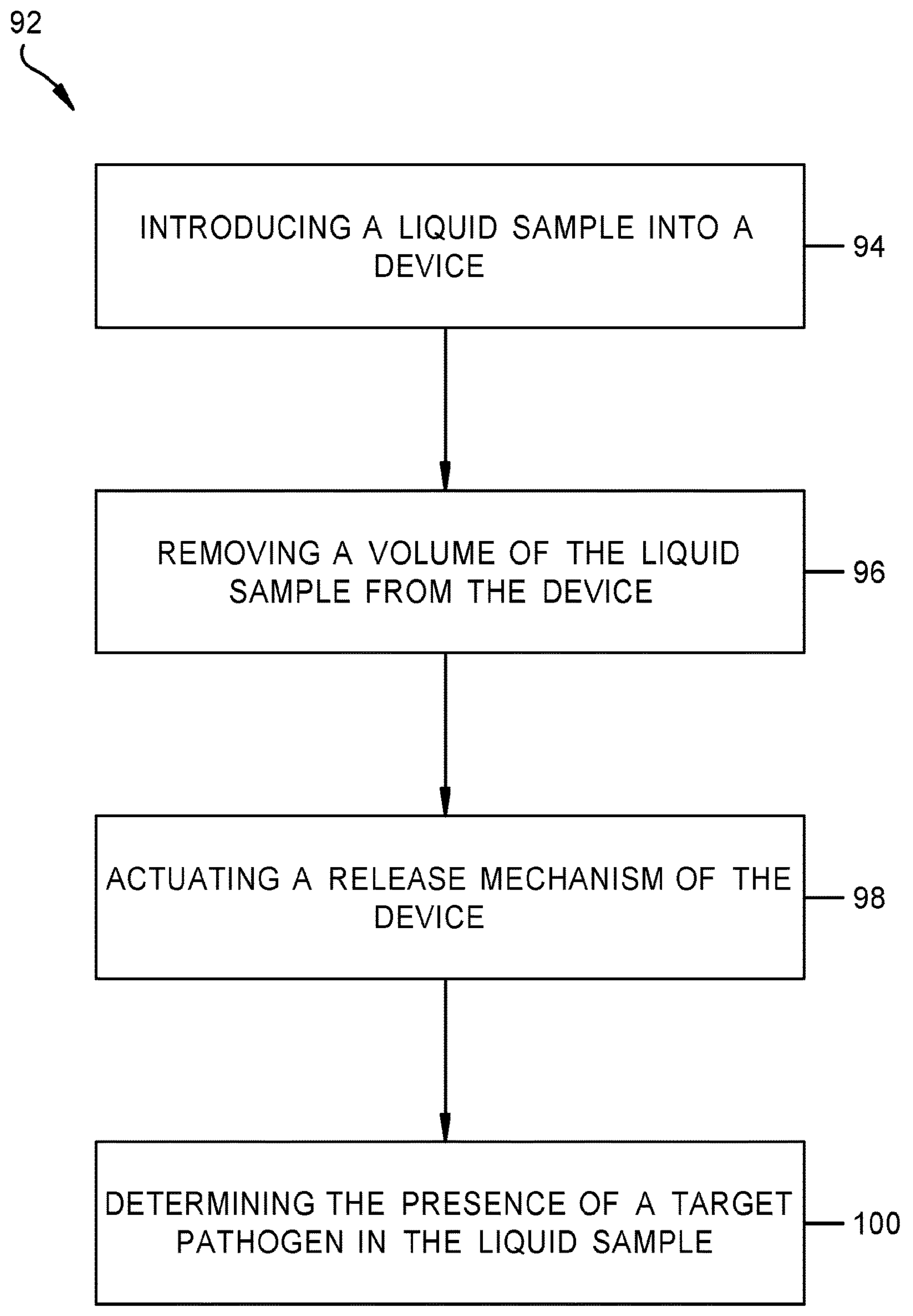
FIG. 17 is a process flow diagram illustrating a method for detecting a target pathogen in a liquid sample according to another aspect of the present disclosure.

One example of the method 74 is illustrated in FIG. 17 and can include a method 92 for detecting a target pathogen, or a biomolecule associated therewith, in a liquid sample. Generally, the method 92 can include the following steps: introducing, through an inlet 16 of a device 10, a liquid sample either before, during, or after introduction of a fluorescent probe specific to the target pathogen, or biomolecule associated therewith, through the inlet (Step 94); removing, from an outlet 18 of the device, a volume of the liquid sample to cause a target pathogen, or biomolecule associated therewith, if present, to be retained on a surface 22 of a filter 20 associated with the outlet (Step 96); actuating a release mechanism 14 of the device to cause release of the retained target pathogen, or biomolecule associated therewith, off of the surface of the filter (Step 98); and determining, by fluoroscopy, the presence of the target pathogen, or biomolecule associated therewith, in the liquid sample (Step 100).

For the purpose of illustration only, the method 92 will be described below in terms of determining antibiotic susceptibility in a subject. Currently, to determine antibiotic susceptibility, bacteria are first partially classified and then analysis for antibiotic susceptibility is performed later due to the time and resources (e.g., a microbiological laboratory) needed to so. As discussed in more detail below, the method 92 of the present disclosure advantageously enables bacteria to be grown in different types of antibiotics, and the rate of growth rapidly determined, by simplifying and reducing the time required for bacterial detection. This, in turn, permits rapid antibiotic susceptibility testing to help medical personnel quickly guide medical treatment.

The method 92 can be performed using a device 10 that is similarly or identically constructed as the device illustrated in FIGS. 1-4 and described above. The method 92 can begin by identifying a subject having, or being suspected of having, a bacterial infection (e.g., based on symptoms, exposure to a particular environment or other infected person, etc.). A liquid sample, such as blood, can be obtained from the subject and then loaded into the inlet 16 of the device 10 before, during, or after introduction of a fluorescent probe (Step 94). The fluorescent probe can specifically bind to a particular bacterium, a biomolecule produced by a particular bacterium, or a reaction product generated by a biomolecule produced by a particular bacterium. In some instances, the liquid sample can be processed prior to loading into the inlet 16. For example, a blood sample can be exposed to a lysing solution to lyse red blood cells present in the sample. The liquid sample can be loaded directly into the inlet 16 by inserting a needle 84 through the septum 36 and dispensing the liquid sample into the interior 38 thereof.

Before the liquid sample is loaded into the inlet 16, the plug member 48 comprising the release mechanism 14 can be situated in a first position (as described above). In the first position, a retention force is applied to the liquid sample to create a first threshold T1 whereby the liquid sample contacts substantially the entire surface 22 of the outlet filter 20 but not an upper surface 86 of the channel 26 adjacent the outlet filter.

Next, the liquid sample can be flowed into the channel 26 through the inlet filter 40 and into the outlet 18 by applying suction or a vacuum to the outlet (e.g., by inserting a suction device 88 through the vacuum gasket 44 into the interior 46 of the outlet). Suction can then be applied to the outlet 18 to remove a volume of the liquid sample (Step 96). As the liquid sample flows through the channel 26 into the outlet 18, certain particles (e.g., red blood cells) can be captured by the inlet filter 40 and prevented from entering the channel while the target bacteria, if present, can pass into the channel.

All, or substantially all, of the liquid sample can be drawn through the outlet 18 and removed by the suction device 88. As the liquid sample is withdrawn, the target bacteria, if present, can accumulate on the surface 22 of the outlet filter 20. Accumulation of the target bacterium effectively concentrates the bacteria, thereby removing the need to separately concentrate the bacteria (e.g., by culturing). In some instances, the target pathogen can accumulate on the surface 22 of the outlet filter 20 and form a substantially continuous layer thereon.

If it has not been done so already, a liquid containing the fluorescent probe can be introduced into the device 10. The liquid containing the fluorescent probe can be added in an amount and for a time sufficient to permit binding of the fluorescent probe with the target pathogen, or a biomolecule associated therewith. After a desired period of time, the release mechanism 14 can be actuated (as described above) (Step 98). Movement of the plug member 48 to the second position causes the liquid sample to move from the first threshold T1 to a second threshold T2. As the liquid sample flows to the second threshold T2, the target pathogen retained on the surface 22 of the outlet filter 20 are displaced off of the outlet filter to a location suitable for detection.

The presence of the target pathogen, or biomolecule associated therewith, in the liquid sample can then be determined (Step 100). For example, a light can be applied to the concentrated pathogen from the lower surface 32 of the housing 12. The fluorescent probe can absorb the light and emit a different color of light, which is then detected by a photodetector. Advantageously, detection of the target bacteria, or biomolecule associated therewith, is highly sensitive because the labeled bacteria are not associated with the outlet filter 20, which is a significant source of autofluorescence. This, in turn, significantly increases resolution of the fluorescence signal being detected. The detected signal can be analyzed to provide information (e.g., quantity or enzymatic characteristics) about the captured target pathogen, or biomolecule associated therewith, which can then be used to determine antibiotic susceptibility.

The inventors have discovered, for example, that the methods described herein can provide a multi-fold decrease in background fluorescence, which advantageously results in a corresponding multi-fold increase in sensitivity/limit of detection. In some instances, the method can provide a 1-fold, 2-fold, 3-fold, 4-fold, 5-fold, 6-fold, 7-fold, or greater decrease in background fluorescence, which results in a 1-fold, 2-fold, 3-fold, 4-fold, 5-fold, 6-fold, 7-fold, or greater increase, respectively, in sensitivity/limit of detection. Further, the methods described herein advantageously permit significantly faster target analyte detection as compared to conventional assays. For example, the color-based Nitrocefin test for beta-Lactamase requires $1\times10^7$ CFU of pathogen for detection in 10 minutes. The devices and methods of the present disclosure only require $1\times10^4$ CFU, so ~1000× enhancement in speed or sensitivity is provided. That is to say, with Nitrocefin, to detect $1\times10^4$ CFU of a beta-lactamase-positive pathogen, it would take 1000×15 minutes, or approximately 250 hours.

The following examples are for the purpose of illustration only and are not intended to limit the scope of the claims, which are appended hereto.

Example 1

Reagents for β-LEAF Assay, Bacterial Strains and Culture Conditions

β-LEAF Bodipy-FL probe was utilized for all experiments.

Antibiotics: Cefazolin-sodium was purchased from Sigma-Aldrich (St. Louis, Mo., USA) and cefoxitin-sodium and cefepime-HCl were obtained from USP-Pharmacopeia.

*S. aureus* strains used in this study were purchased from ATCC (Manassas, Va., USA) (Table 2)

TABLE 2

*S. aureus* strains and isolates used in this study

| # | *S. aureus* isolate | Source |
|---|---|---|
| 1 | 29213 [β-lactamase (+)] | ATCC |
| 2 | 25923 [β-lactamase (−)] | ATCC |

ATCC = American Type Culture Collection

Bacteria were cultured using Brain Heart Infusion (BHI) media. BHI broth and BHI agar were obtained from BD Difco (BD: Becton, Dickinson and Company, New Jersey, USA). Penicillin disks (10U) were purchased from BD BBL. All strains were routinely cultured in BHI agar or broth at 37° C. The isolates were grown in presence of penicillin disks to induce and enhance β-lactamase production as required. Frozen bovine cerebral spinal fluid was acquired from BioreclamationIVT (Westbury, N.Y. USA).

Device Fabrication

Figure 18A:
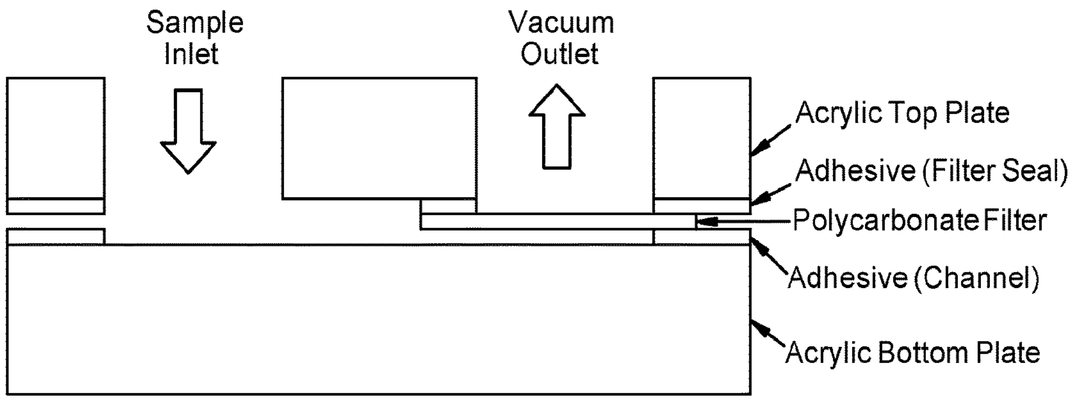
FIG. 18A is a cross-sectional view showing a device for detecting a target analyte in a liquid sample constructed in accordance with another aspect of the present disclosure.
Figure 18B:
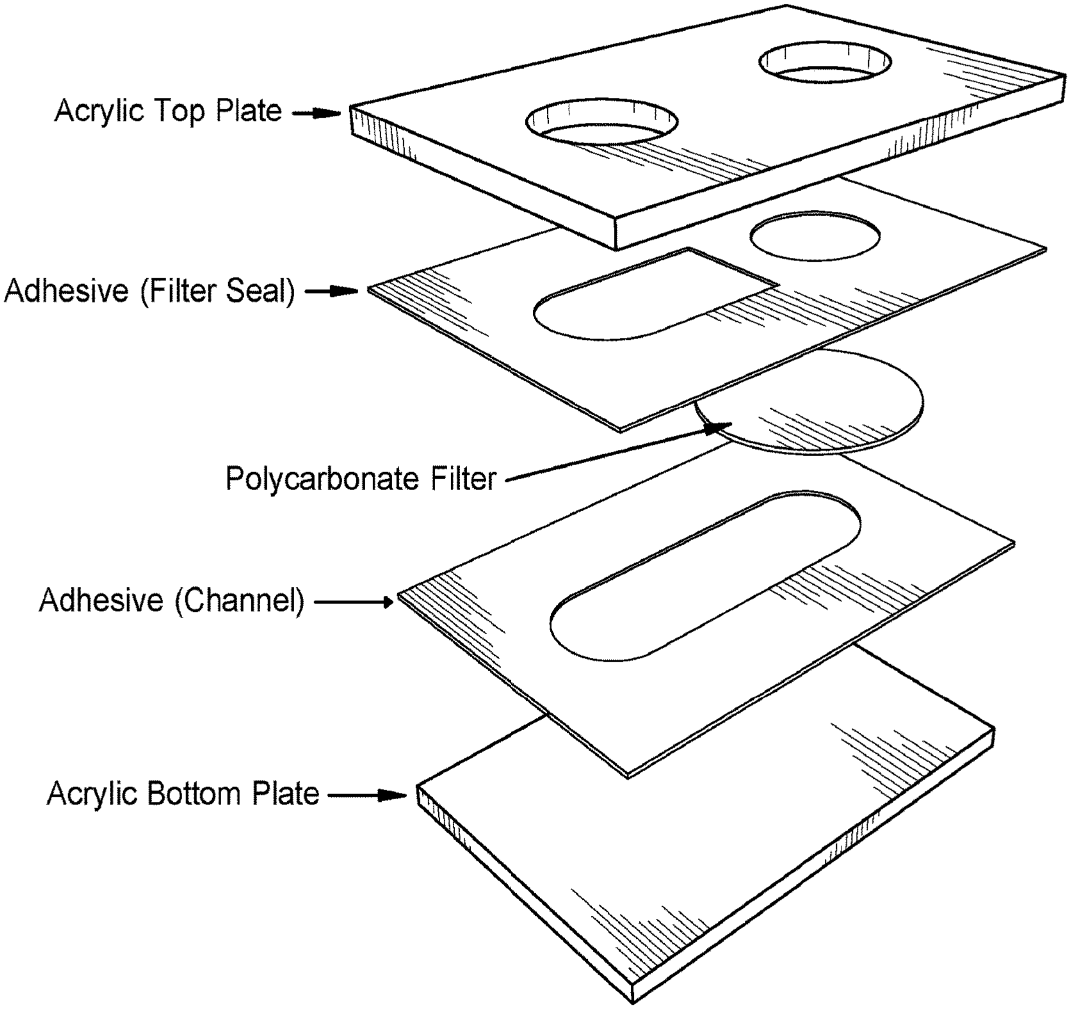
FIG. 18B is an exploded perspective view of the device in FIG. 18A.
Figure 18C:
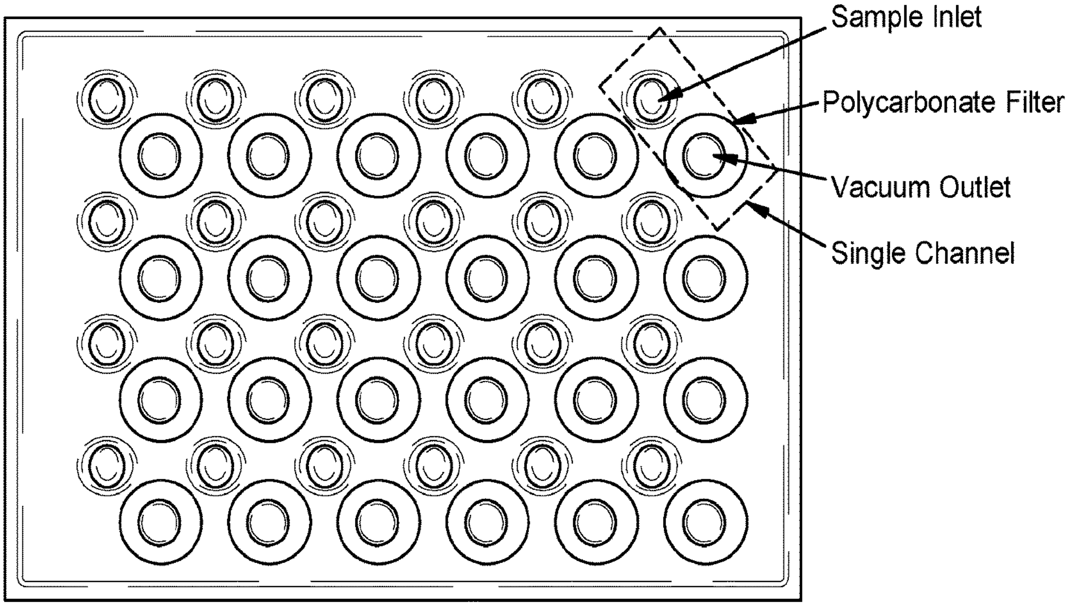
FIG. 18C is a top view of the device in FIGS. 18A-B.

Device fabrication is illustrated in FIGS. 18A-C. 1/16" clear acrylic was purchased from McMaster-Carr (Princeton, N.J. USA) and 3M 8212 double sided adhesive from LightFab (Rochester, N.Y., USA). These materials were cut using a 50 W $CO_2$ laser from Universal Laser Systems (VLS 3.50; Scottsdale, Ariz., USA). 400 nm pore size, 13 mm diameter, nuclear track-etched polycarbonate black filters were purchased from Sterlitech (Kent, Wash., USA). The filters, acrylic sheets and double sided adhesive were assembled by hand. Each device plate was fabricated in the dimensions of an ordinary microtiter plate for use in standard fluorescence plate readers and contained 24 individual channels.

β-LEAF Assays

Preparation of bacterial sample: bacterial strains were cultured on BHI agar plates in the presence of a penicillin disk (10 U) overnight. For each bacterial isolate, colonies closest to the penicillin disk were transferred to PBS to make a homogenous suspension. Bacterial O.D. was measured at 600 nm. Required dilutions were further prepared in PBS.

For bio-specimen testing, bacteria were spiked in cerebrospinal fluid (bovine source) or serum (fetal calf serum) at known concentrations, and used as the bacterial sample solutions.

β-LEAF Assays on the Device

Figure 19:
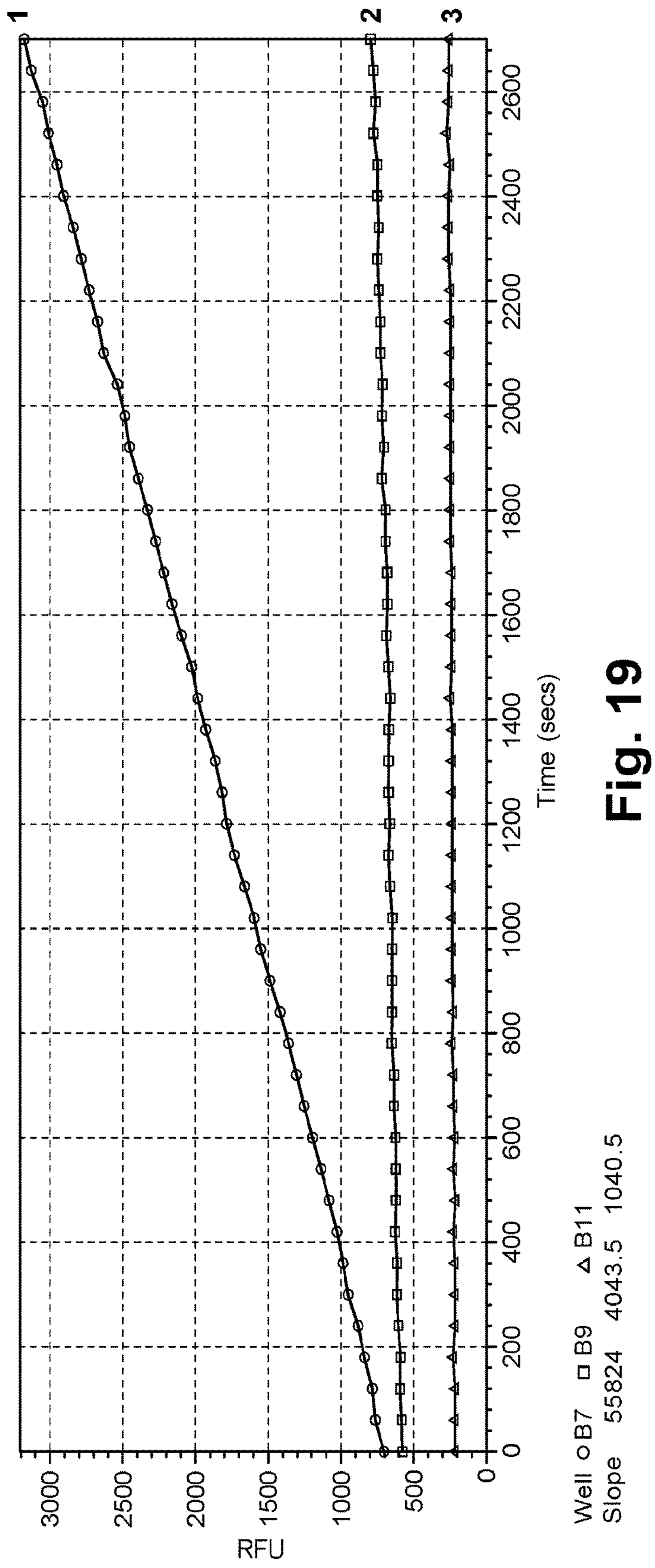
FIG. 19 is a graph showing the results of a beta-Lactamase Enzyme Activated Fluorophore (β-LEAF) assay using the device in FIGS. 18A-C (1=*S. aureus* ATCC 29213 (β-lactamase producer); 2=*S. aureus* ATCC 25923 (β-lactamase non-producer); and 3=PBS)
Figure 20:
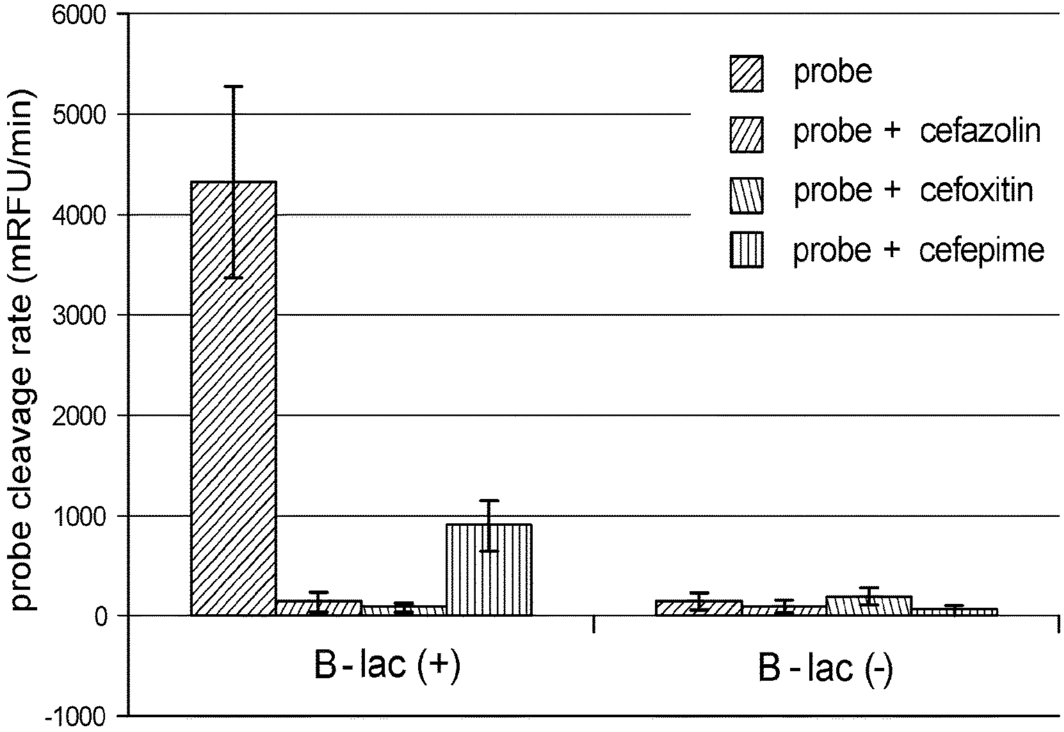
FIG. 20 is a graph showing the results of the β-LEAF assay with antibiotics. For this experiment, $4\times10^8$ CFU/ml bacterial solution was prepared in PBS, 250 μl of the solution was filtered through, and the total bacteria in each reaction was $10^8$ CFU (β-lac (+)=*S. aureus* ATCC 29213 (β-lactamase producer); β-lac (−)=*S. aureus* ATCC 25923 (β-lactamase non-producer); averages with standard error shown; data representative of 5 independent experiments)
Figure 21:
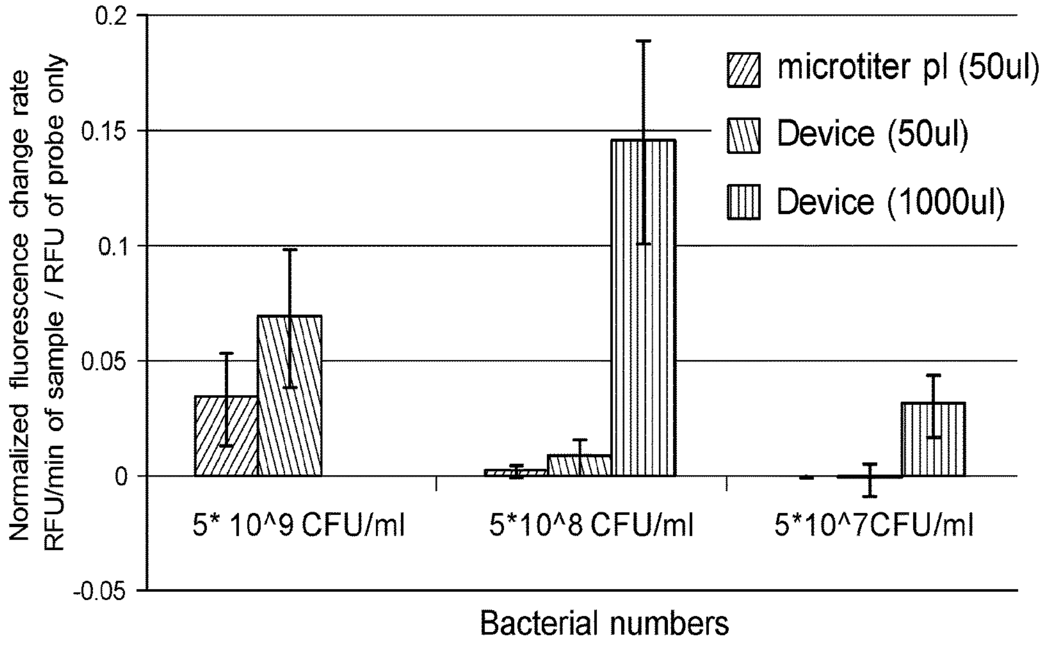
FIG. 21 is a graph showing a comparison of the β-LEAF assay using the device in FIGS. 18A-C and a 96-well microtiter plate (averages with standard error shown; data representative of 2 independent experiments) (note: 5*10^9 CFU/ml: 50 μl=$10^8$ CFU; 1000 μl=$5\times10^9$ CFU; 5*10^8 CFU/ml: 50 μl=$10^7$ CFU; 1000 μl=$5\times10^8$ CFU; and 5*10^7 CFU/ml: 50 μl=$10^6$ CFU; 1000 μl=$5\times10^7$ CFU)
Figure 22:
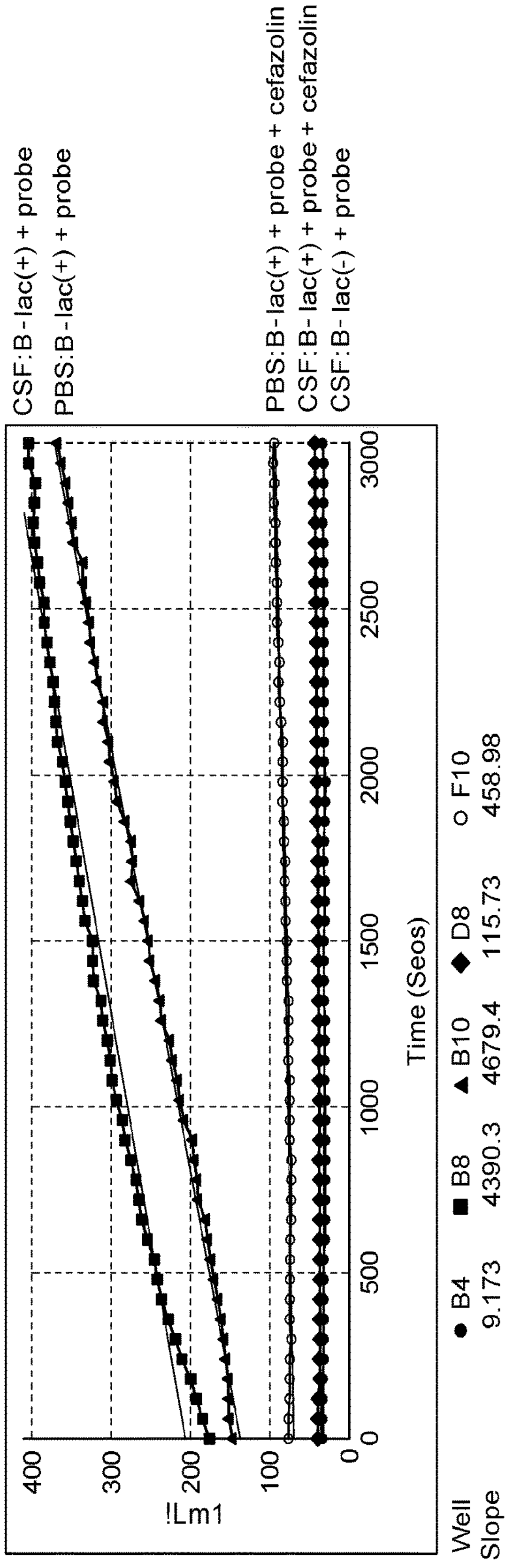
FIG. 22 is a graph showing β-LEAF assay results in bovine cerebrospinal fluid (CSF)
Figure 23:
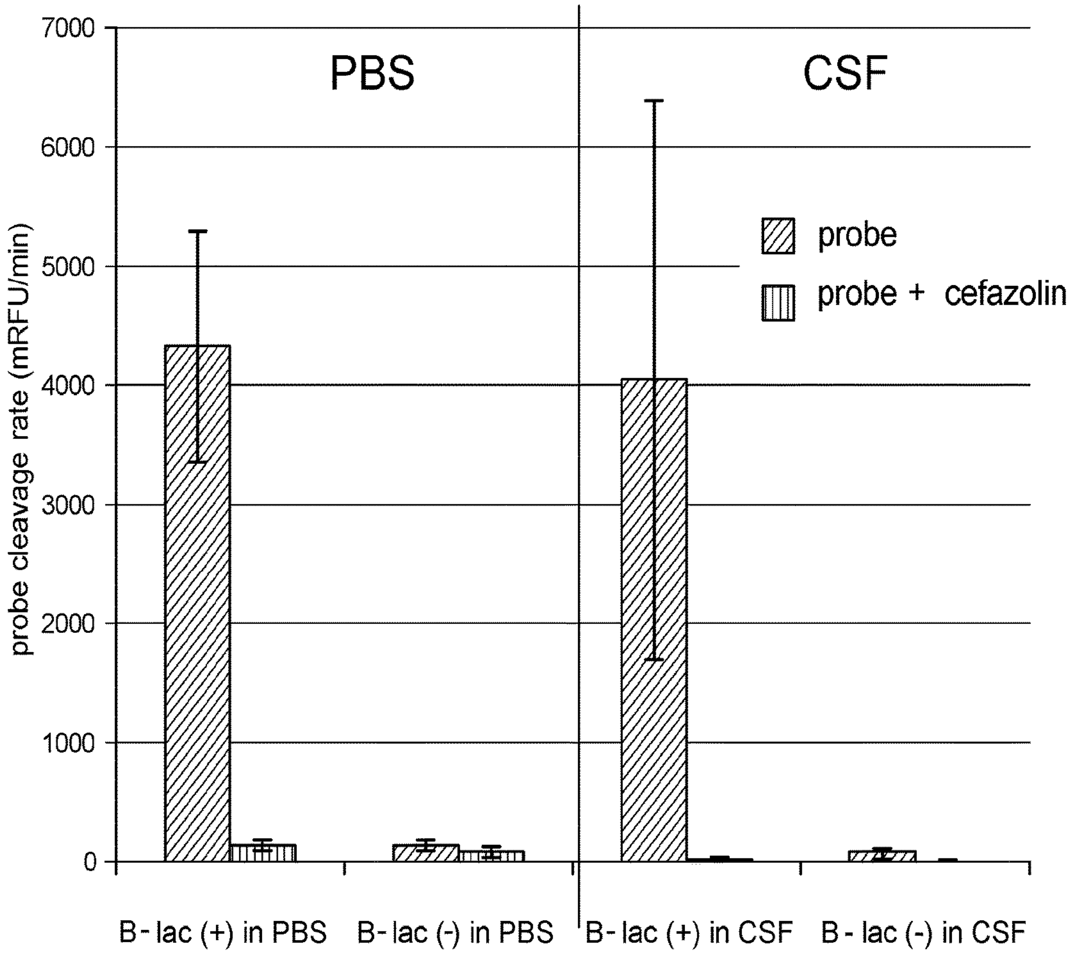
FIG. 23 is a graph showing β-LEAF assay results in bovine CSF and PBS (averages with standard error shown; data representative of 3 independent experiments)
Figure 24:
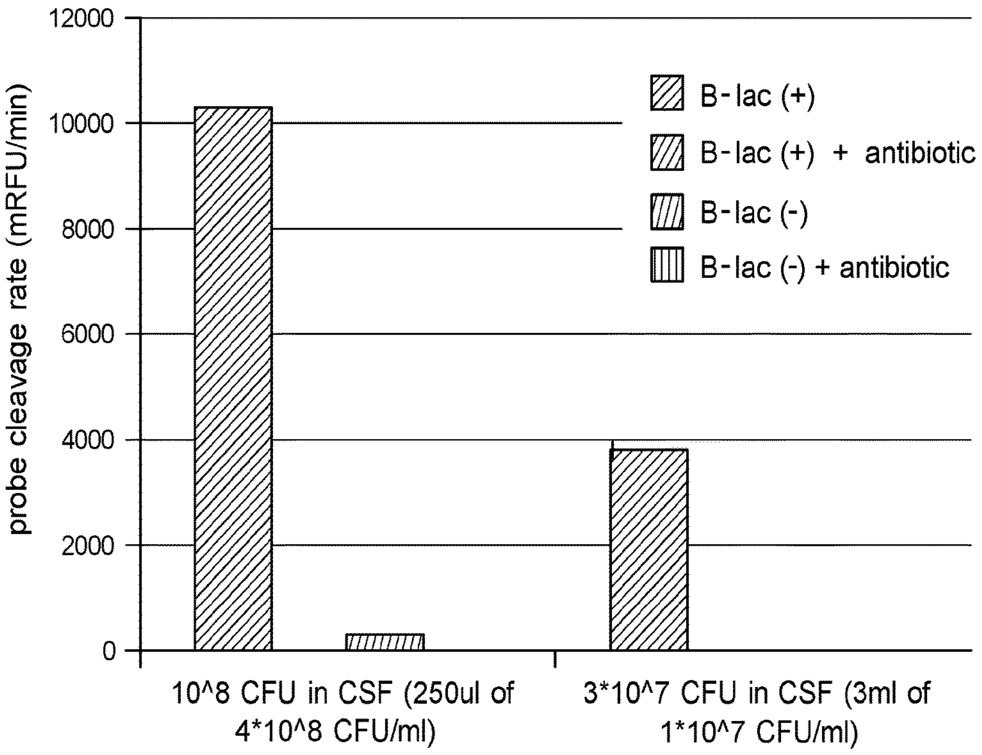
FIG. 24 is a graph showing β-LEAF assay results in bovine CSF with different bacterial concentrations.

For probe only reactions (FIG. 19), 10 μM β-LEAF probe in 20% DMSO in PBS was prepared. For probe+antibiotic reactions (FIG. 20), a solution mix of 10 μM β-LEAF probe and 25 mM antibiotic in 20% DMSO in PBS was prepared (antibiotic stock solutions were prepared by dissolving the respective antibiotic powders in PBS).

To perform the assays on the device, each reaction was set up in an individual channel. Fluid was driven through the device by applying vacuum to the vacuum outlet port of the device. Solutions were added sequentially through the inlet in the following order: 100 μl of PBS was filtered, followed by the desired volume of bacterial solution of known concentration. Thereafter 100 μl of (probe only) or (probe+antibiotic) solution was filtered through with incomplete suction. The device was placed in the plate reader (Spectramax M5 Plate Reader, Molecular Devices) and time course assays were carried out, monitoring β-LEAF cleavage by measuring fluorescence for 60 min, at 1 min intervals. Instrument settings were kept as excitation at 450 nm, emission at 510 nm, with fluorescence read from the bottom in accordance with device design and filter placement in the channels. Temperature was maintained at 37° C. throughout. β-LEAF cleavage rate in each case was determined as slope, i.e., fluorescence change as a function of time (obtained from instrument software—SoftMax Pro 6.3).

β-LEAF Assays on 96-well Microtiter Plates (for Comparing with Assay Efficiency on Device).

20 μM β-LEAF probe solution (2× stock) was prepared in 40% DMSO in PBS. The assays were performed in 96-well white clear-bottom plates in a total volume of 100 μl respectively, to include bacteria and 10 μM β-LEAF probe. Each reaction was set up with 50 μl bacterial suspension and 50 μl probe 2× stock solution, with resultant buffer concentration as 20% DMSO in PBS in each 100 μl reaction. Reactions were performed in duplicate. Time course assays were carried out, monitoring β-LEAF cleavage by measuring fluorescence for 60 min, at 1 min intervals (Spectramax M5 Plate Reader, Molecular Devices). Instrument settings were kept as excitation at 450 nm, emission at 510 nm. Temperature was maintained at 37° C. throughout. β-LEAF cleavage rate in each case was determined as slope, i.e., fluorescence change as a function of time (obtained from instrument software—SoftMax Pro 6.3). Results of the β-LEAF assays on 96-well microtiter plates are shown in FIGS. 21-24.

From the above description of the present disclosure, those skilled in the art will perceive improvements, changes and modifications. For example, it will be appreciated that the devices 10 and 52 can have a multi-layer configuration similar or identical to the multi-layer configuration of the device 112. Such improvements, changes, and modifications are within the skill of those in the art and are intended to be covered by the appended claims. All patents, patent applications, and publication cited herein are incorporated by reference in their entirety.

The following is claimed:

1. A method for detecting a target analyte in a liquid sample, the method comprising the steps of:

introducing, through an inlet of a device, a liquid sample either before, during, or after introduction of a detection reagent, the device including a flow system comprising at least one channel that is in communication with the inlet and an outlet, at least a portion of the at least one channel being located substantially adjacent a surface of a filter associated with the outlet, the filter having pores having a size that prevents passage of a target analyte into the interior of the outlet but allows passage of the liquid sample therethrough, the at least one channel with a diameter shaped and dimensioned to reduce the amount of unreacted detection reagent available to create background interference during detection;

suctioning, from the outlet, a volume of the liquid sample to cause the target analyte, if present, to be retained on the surface of the filter;

exposing the target analyte to a detection reagent specific to the target analyte; and detecting the presence of the target analyte in the liquid sample.

2. The method of claim 1, wherein the target analyte is a target pathogen or biomolecule associated therewith.

3. The method of claim 1, wherein the detection reagent is a fluorescent probe specific to the target pathogen or biomolecule associated therewith.

4. The method of claim 3, wherein the fluorescent probe is beta-Lactamase Enzyme Activated Fluorophore (β-LEAF) and the target pathogen is *S. aureus*.

5. The method of claim 1, wherein the target analyte, if present, is concentrated on the surface of the filter associated with the outlet such that the concentration is greater than the concentration of the target analyte in the liquid sample.

6. A method for detecting a target pathogen, or biomolecule associated therewith, in a liquid sample, the method comprising the steps of:

introducing, through an inlet of a housing of a device, a liquid sample either before, during, or after introduction of a fluorescent probe specific to the target pathogen, or biomolecule associated therewith;

suctioning, from an outlet of the device, a volume of the liquid sample to cause a target pathogen, or biomolecule associated therewith, if present, to be retained on a surface of a filter associated with the outlet, the filter having pores having a size that prevents passage of the target pathogen, or biomolecule associated therewith, into the interior of the outlet but allows passage of the liquid sample therethrough;

retracting a plug member that is slidably disposed in a second outlet of the housing and that blocks liquid sample flow in a non-retracted position, axially away from the housing so that the liquid sample flows through the flow system towards the second outlet to cause release of the retained target pathogen, or biomolecule associated therewith, off of the surface of the filter; and determining, by fluoroscopy, the presence of the target pathogen, or biomolecule associated therewith, in the liquid sample;

whereby release of the target pathogen, or biomolecule associated therewith, reduces background fluorescence associated with the fluorescent probe during the determining step.

7. The method of claim 6, wherein the fluorescent probe is β-LEAF and the target pathogen is *S. aureus*.

8. The method of claim 6, wherein the target pathogen or biomolecule associated therewith, if present, is concentrated on the surface of the filter associated with the outlet such that the concentration is greater than the concentration of the target pathogen or biomolecule associated therewith in the liquid sample.

* * * * *